United States Patent
McAfee et al.

(10) Patent No.: US 11,147,673 B2
(45) Date of Patent: Oct. 19, 2021

(54) PERCUTANEOUS PAPILLARY MUSCLE RELOCATION

(71) Applicant: BOSTON SCIENTIFIC SCIMED, INC., Maple Grove, MN (US)

(72) Inventors: Patricia McAfee, Galway (IE); Sean O'Sullivan, Galway (IE); Tim O'Connor, Galway (IE); Aiden Flanagan, County Galway (IE); Ewa Klusak, Galway (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 194 days.

(21) Appl. No.: 16/419,640

(22) Filed: May 22, 2019

(65) Prior Publication Data
US 2019/0358037 A1    Nov. 28, 2019

Related U.S. Application Data

(60) Provisional application No. 62/675,118, filed on May 22, 2018.

(51) Int. Cl.
*A61F 2/24*    (2006.01)
*A61B 17/00*   (2006.01)
(Continued)

(52) U.S. Cl.
CPC ...... *A61F 2/2466* (2013.01); *A61B 17/00234* (2013.01); *A61B 17/0469* (2013.01);
(Continued)

(58) Field of Classification Search
CPC .... A61F 2/2466; A61F 2/2457; A61F 2/2454; A61F 2/2487
See application file for complete search history.

(56) References Cited

U.S. PATENT DOCUMENTS

| 3,130,418 A | 4/1964 | Head et al. |
| 5,415,667 A | 5/1995 | Frater |

(Continued)

FOREIGN PATENT DOCUMENTS

| AU | 2015200387 B2 | 11/2016 |
| CN | 102579161 A | 7/2012 |

(Continued)

OTHER PUBLICATIONS

International Search Report and Written Opinion dated Sep. 18, 2019 for International Application No. PCT/US2019/033572.

*Primary Examiner* — Suba Ganesan
(74) *Attorney, Agent, or Firm* — Seager, Tufte & Wickhem LLP

(57) ABSTRACT

A system for treating mitral regurgitation may include an outer sheath having a lumen extending to a distal end of the outer sheath, an intermediate sheath slidably disposed within the lumen of the outer sheath, the intermediate sheath having a lumen extending to a distal end of the intermediate sheath, and an inner sheath slidably disposed within the lumen of the intermediate sheath, wherein the inner sheath includes a first anchor disposed within a lumen of the inner sheath, the first anchor being configured to penetrate and secure to a first papillary muscle. The intermediate sheath may include a tissue grasping mechanism at the distal end of the intermediate sheath, the tissue grasping mechanism being configured to hold and stabilize the first papillary muscle for penetration and securement of the first anchor to the first papillary muscle.

15 Claims, 22 Drawing Sheets

(51) Int. Cl.
*A61B 17/04* (2006.01)
*A61B 17/30* (2006.01)
(52) U.S. Cl.
CPC ............ *A61B 17/30* (2013.01); *A61F 2/2487* (2013.01); *A61B 2017/00243* (2013.01); *A61F 2/2463* (2013.01); *A61F 2220/0016* (2013.01); *A61F 2220/0075* (2013.01); *A61F 2250/0007* (2013.01)

(56) References Cited

U.S. PATENT DOCUMENTS

| | | | |
|---|---|---|---|
| 5,480,424 | A | 1/1996 | Cox |
| 5,554,184 | A | 9/1996 | Machiraju |
| 5,662,704 | A | 9/1997 | Gross |
| 5,824,063 | A | 10/1998 | Cox |
| 5,824,067 | A | 10/1998 | Gross |
| 5,910,169 | A | 6/1999 | Peredo |
| 5,931,868 | A | 8/1999 | Gross |
| 5,989,284 | A | 11/1999 | Laufer |
| 6,074,417 | A | 6/2000 | Peredo |
| 6,136,017 | A | 10/2000 | Craver et al. |
| 6,267,781 | B1 | 7/2001 | Tu |
| 6,306,133 | B1 | 10/2001 | Tu et al. |
| 6,358,277 | B1 | 3/2002 | Duran |
| 6,409,759 | B1 | 6/2002 | Peredo |
| 6,719,788 | B2 | 4/2004 | Cox |
| 6,740,107 | B2 | 5/2004 | Loeb et al. |
| 6,945,996 | B2 | 9/2005 | Sedransk |
| 7,087,079 | B2 | 8/2006 | Navia et al. |
| 7,316,712 | B2 | 1/2008 | Peredo |
| 7,331,972 | B1 | 2/2008 | Cox |
| 7,361,137 | B2 | 4/2008 | Taylor et al. |
| 7,488,346 | B2 | 2/2009 | Navia |
| 7,591,847 | B2 | 9/2009 | Navia et al. |
| 7,608,091 | B2 | 10/2009 | Goldfarb et al. |
| 7,635,329 | B2 | 12/2009 | Goldfarb et al. |
| 7,635,386 | B1 | 12/2009 | Gammie |
| 7,693,563 | B2 | 4/2010 | Suresh et al. |
| 7,753,923 | B2 | 7/2010 | St. Goar et al. |
| 7,799,038 | B2 | 9/2010 | Sogard et al. |
| 7,871,433 | B2 | 1/2011 | Lattouf |
| 7,998,151 | B2 | 8/2011 | St. Goar et al. |
| 8,029,565 | B2 | 10/2011 | Lattouf |
| 8,043,368 | B2 | 10/2011 | Crabtree |
| 8,052,592 | B2 | 11/2011 | Goldfarb et al. |
| 8,100,820 | B2 | 1/2012 | Hauser et al. |
| 8,157,719 | B1 | 4/2012 | Ainsworth et al. |
| 8,187,299 | B2 | 5/2012 | Goldfarb et al. |
| 8,226,711 | B2 | 7/2012 | Mortier et al. |
| 8,236,049 | B2 | 8/2012 | Rowe et al. |
| 8,292,884 | B2 | 10/2012 | Levine et al. |
| 8,323,334 | B2 | 12/2012 | Deem et al. |
| 8,323,335 | B2 | 12/2012 | Rowe et al. |
| 8,328,798 | B2 | 12/2012 | Witzel et al. |
| 8,398,708 | B2 | 3/2013 | Meiri et al. |
| 8,431,397 | B2 | 4/2013 | Robinson et al. |
| 8,449,599 | B2 | 5/2013 | Chau et al. |
| 8,545,551 | B2 | 10/2013 | Loulmet |
| 8,585,755 | B2 | 11/2013 | Chau et al. |
| 8,597,348 | B2 | 12/2013 | Rowe et al. |
| 8,608,797 | B2 | 12/2013 | Gross et al. |
| 8,685,083 | B2 | 4/2014 | Perier et al. |
| 8,734,505 | B2 | 5/2014 | Goldfarb et al. |
| 8,758,393 | B2 | 6/2014 | Zentgraf |
| 8,778,016 | B2 | 7/2014 | Janovsky et al. |
| 8,784,483 | B2 | 7/2014 | Navia |
| 8,828,040 | B2 | 9/2014 | Goff |
| 8,845,719 | B2 | 9/2014 | Matheny |
| 8,852,213 | B2 | 10/2014 | Gammie et al. |
| 8,870,950 | B2 | 10/2014 | Hacohen |
| 8,920,322 | B2 | 11/2014 | Mansi et al. |
| 8,926,691 | B2 | 1/2015 | Chau et al. |
| 8,956,406 | B2 | 2/2015 | Subramanian et al. |
| 8,968,393 | B2 | 3/2015 | Rothstein |
| 8,986,370 | B2 | 3/2015 | Annest |
| 8,986,371 | B2 | 3/2015 | Quill et al. |
| 8,992,604 | B2 | 3/2015 | Gross et al. |
| 8,992,606 | B2 | 3/2015 | Ruyra Baliarda |
| 9,011,522 | B2 | 4/2015 | Annest |
| 9,023,099 | B2 | 5/2015 | Duffy et al. |
| 9,050,188 | B2 | 6/2015 | Schweich, Jr. et al. |
| 9,084,676 | B2 | 7/2015 | Chau et al. |
| 9,125,738 | B2 | 9/2015 | Figulla et al. |
| 9,155,622 | B2 | 10/2015 | Ruyra Baliarda et al. |
| 9,241,790 | B2 | 1/2016 | Lane et al. |
| 9,248,014 | B2 | 2/2016 | Lane et al. |
| 9,254,190 | B2 | 2/2016 | Gurskis |
| 9,421,094 | B2 | 8/2016 | Schweich, Jr. et al. |
| 9,427,315 | B2 | 8/2016 | Schweich, Jr. et al. |
| 9,433,500 | B2 | 9/2016 | Chau et al. |
| 9,468,528 | B2 | 10/2016 | Starksen et al. |
| 9,486,281 | B2 | 11/2016 | Fung et al. |
| 9,526,613 | B2 | 12/2016 | Gross et al. |
| 9,539,094 | B2 | 1/2017 | Dale et al. |
| 9,579,196 | B2 | 2/2017 | Morriss et al. |
| 9,579,200 | B2 | 2/2017 | Lederman et al. |
| 9,585,632 | B2 | 3/2017 | Kanik et al. |
| 9,603,709 | B2 | 3/2017 | Call et al. |
| 9,615,925 | B2 | 4/2017 | Subramanian et al. |
| 9,629,720 | B2 | 4/2017 | Nguyen et al. |
| 9,681,951 | B2 | 6/2017 | Ratz et al. |
| 9,700,413 | B2 | 7/2017 | Ruyra Baliarda et al. |
| 9,713,529 | B2 | 7/2017 | Lane et al. |
| 9,744,036 | B2 | 8/2017 | Duffy et al. |
| 9,750,607 | B2 | 9/2017 | Ganesan et al. |
| 9,770,329 | B2 | 9/2017 | Lane et al. |
| 9,775,709 | B2 | 10/2017 | Miller et al. |
| 9,795,482 | B2 | 10/2017 | Duffy et al. |
| 9,844,435 | B2 | 12/2017 | Eidenschink |
| 9,877,833 | B1 | 1/2018 | Bishop et al. |
| 9,895,225 | B2 | 2/2018 | Rolando et al. |
| 9,949,829 | B2 | 4/2018 | Starksen et al. |
| 9,993,338 | B2 | 6/2018 | Rowe et al. |
| 10,010,417 | B2 | 7/2018 | Keidar |
| 10,034,749 | B2 | 7/2018 | Spence et al. |
| 10,039,644 | B2 | 8/2018 | Navia et al. |
| 10,052,198 | B2 | 8/2018 | Chau et al. |
| 10,052,199 | B2 | 8/2018 | Spence et al. |
| 10,064,405 | B2 | 9/2018 | Dale et al. |
| 10,064,718 | B2 | 9/2018 | Keidar |
| 10,111,747 | B2 | 10/2018 | Gifford, III |
| 10,179,044 | B2 | 1/2019 | Ratz et al. |
| 10,195,026 | B2 | 2/2019 | Karapetian et al. |
| 10,195,028 | B2 | 2/2019 | Hosmer et al. |
| 10,213,305 | B2 | 2/2019 | Solem et al. |
| 10,219,903 | B2 | 3/2019 | Subramanian et al. |
| 10,226,330 | B2 | 3/2019 | Spence et al. |
| 10,231,834 | B2 | 3/2019 | Keidar |
| 10,238,490 | B2 | 3/2019 | Gifford, III |
| 10,285,686 | B2 | 5/2019 | Gammie et al. |
| 10,292,816 | B2 | 5/2019 | Raanani et al. |
| 10,297,027 | B2 | 5/2019 | Scutaru et al. |
| 10,327,743 | B2 | 6/2019 | St. Goar et al. |
| 10,363,392 | B2 | 7/2019 | Legaspi et al. |
| 10,368,988 | B2 | 8/2019 | Jones |
| 10,405,977 | B2 | 9/2019 | Solem |
| 10,405,981 | B2 | 9/2019 | Hjelle et al. |
| 2003/0078653 | A1 | 4/2003 | Vesely et al. |
| 2004/0039442 | A1 | 2/2004 | St Goar et al. |
| 2004/0186566 | A1 | 9/2004 | Hindrichs et al. |
| 2005/0043609 | A1 | 2/2005 | Murphy et al. |
| 2005/0075727 | A1 | 4/2005 | Wheatley |
| 2005/0159810 | A1 | 7/2005 | Filsoufi |
| 2006/0095025 | A1 | 5/2006 | Levine et al. |
| 2006/0195182 | A1 | 8/2006 | Navia et al. |
| 2007/0038294 | A1 | 2/2007 | Navia |
| 2007/0118151 | A1 | 5/2007 | Davidson |
| 2007/0208297 | A1 | 9/2007 | Ainsworth et al. |
| 2008/0039935 | A1 | 2/2008 | Such et al. |
| 2008/0119882 | A1 | 5/2008 | Cox |
| 2008/0161638 | A1 | 7/2008 | Taylor et al. |
| 2008/0167714 | A1 | 7/2008 | St Goar et al. |
| 2008/0195126 | A1 | 8/2008 | Solem |

(56) References Cited

U.S. PATENT DOCUMENTS

| | | |
|---|---|---|
| 2009/0043381 A1 | 2/2009 | MacOviak et al. |
| 2009/0099410 A1 | 4/2009 | De Marchena |
| 2009/0188964 A1 | 7/2009 | Drlov |
| 2010/0023118 A1 | 1/2010 | Medlock et al. |
| 2010/0198208 A1 | 8/2010 | Napp et al. |
| 2010/0217283 A1 | 8/2010 | St Goar et al. |
| 2010/0262233 A1 | 10/2010 | He |
| 2011/0004297 A1 | 1/2011 | Sogard et al. |
| 2011/0011917 A1* | 1/2011 | Loulmet ............ A61B 17/0401 227/181.1 |
| 2012/0010461 A1 | 1/2012 | Goldfarb et al. |
| 2012/0041548 A1 | 2/2012 | Crabtree |
| 2012/0065498 A1 | 3/2012 | Redel et al. |
| 2013/0110230 A1 | 5/2013 | Solem |
| 2013/0190861 A1 | 7/2013 | Chau et al. |
| 2013/0197630 A1 | 8/2013 | Azarnoush |
| 2014/0066693 A1 | 3/2014 | Gold farb et al. |
| 2014/0257467 A1 | 9/2014 | Lane et al. |
| 2014/0350669 A1 | 11/2014 | Gillespie et al. |
| 2014/0364875 A1 | 12/2014 | Zentgraf |
| 2015/0051698 A1 | 2/2015 | Ruyra Baliarda et al. |
| 2015/0202044 A1 | 7/2015 | Chau et al. |
| 2015/0250590 A1 | 9/2015 | Gries et al. |
| 2015/0313620 A1 | 11/2015 | Suri |
| 2016/0213472 A1 | 7/2016 | Kim |
| 2016/0220785 A1 | 8/2016 | Fabro |
| 2016/0270911 A1 | 9/2016 | Ganesan et al. |
| 2017/0056176 A1 | 3/2017 | Rowe et al. |
| 2017/0105839 A1 | 4/2017 | Subramanian et al. |
| 2017/0135815 A1 | 5/2017 | Gross et al. |
| 2017/0209261 A1 | 7/2017 | Bortlein |
| 2017/0224488 A1 | 8/2017 | Lederman et al. |
| 2017/0231762 A1 | 8/2017 | Quadri et al. |
| 2017/0239048 A1 | 8/2017 | Goldfarb et al. |
| 2017/0252153 A1 | 9/2017 | Chau et al. |
| 2017/0281336 A1 | 10/2017 | Lane et al. |
| 2017/0296168 A1 | 10/2017 | Nobles et al. |
| 2017/0304050 A1 | 10/2017 | Keidar et al. |
| 2017/0319333 A1 | 11/2017 | Tegels et al. |
| 2017/0319340 A1 | 11/2017 | Duffy et al. |
| 2017/0348100 A1 | 12/2017 | Lane et al. |
| 2017/0354496 A1 | 12/2017 | Quadri et al. |
| 2017/0354497 A1 | 12/2017 | Quadri et al. |
| 2017/0360426 A1 | 12/2017 | Hacohen et al. |
| 2017/0367822 A1 | 12/2017 | Naor et al. |
| 2018/0000586 A1 | 1/2018 | Ganesan et al. |
| 2018/0000587 A1 | 1/2018 | Duffy et al. |
| 2018/0028313 A1 | 2/2018 | Rowe et al. |
| 2018/0085218 A1 | 3/2018 | Eidenschink |
| 2018/0116790 A1 | 5/2018 | Ratz et al. |
| 2018/0185150 A1 | 7/2018 | Bishop et al. |
| 2018/0185151 A1 | 7/2018 | Bishop et al. |
| 2018/0185152 A1 | 7/2018 | Bishop et al. |
| 2018/0185153 A1 | 7/2018 | Bishop et al. |
| 2018/0221143 A1 | 8/2018 | Ratz et al. |
| 2018/0235755 A1 | 8/2018 | Quadri et al. |
| 2018/0256324 A1 | 9/2018 | Quadri et al. |
| 2018/0263659 A1 | 9/2018 | Lattouf |
| 2018/0263768 A1 | 9/2018 | Zhang et al. |
| 2018/0289480 A1 | 10/2018 | D'ambra et al. |
| 2018/0289484 A1 | 10/2018 | Kofidis |
| 2018/0303613 A1 | 10/2018 | Maimon et al. |
| 2018/0318082 A1* | 11/2018 | Manash ............ A61B 17/0401 |
| 2018/0353292 A1 | 12/2018 | Keidar |
| 2018/0368977 A1 | 12/2018 | Gorman, III et al. |
| 2019/0000624 A1 | 1/2019 | Wilson et al. |
| 2019/0029812 A1 | 1/2019 | Gifford, III |
| 2019/0029826 A1 | 1/2019 | Zeitani |
| 2019/0060067 A1 | 2/2019 | Keranen et al. |
| 2019/0060070 A1 | 2/2019 | Groothuis et al. |
| 2019/0060071 A1 | 2/2019 | Lane et al. |
| 2019/0076250 A1 | 3/2019 | Hjelle et al. |
| 2019/0091023 A1 | 3/2019 | Starksen et al. |
| 2019/0095589 A1 | 3/2019 | Kim et al. |
| 2019/0110894 A1 | 4/2019 | Braido et al. |
| 2019/0117206 A1 | 4/2019 | Thambar et al. |
| 2019/0151093 A1 | 5/2019 | Keidar et al. |
| 2019/0167421 A1 | 6/2019 | Chau et al. |
| 2019/0167427 A1 | 6/2019 | Gifford, III |
| 2019/0175203 A1 | 6/2019 | Goldfarb et al. |
| 2019/0175337 A1 | 6/2019 | Solem et al. |
| 2019/0183489 A1 | 6/2019 | Gemetta et al. |
| 2019/0183646 A1 | 6/2019 | Keranen |
| 2019/0209325 A1 | 7/2019 | Lattouf |
| 2019/0216601 A1 | 7/2019 | Purcell et al. |
| 2019/0231528 A1 | 8/2019 | MacMahon et al. |
| 2019/0247034 A1 | 8/2019 | Stack et al. |
| 2019/0254816 A1 | 8/2019 | Anderson et al. |
| 2019/0269839 A1 | 9/2019 | Wilson et al. |

FOREIGN PATENT DOCUMENTS

| | | |
|---|---|---|
| CN | 202477903 U | 10/2012 |
| CN | 204336975 U | 5/2015 |
| CN | 104665888 A | 6/2015 |
| CN | 108635017 A | 10/2018 |
| CN | 108904102 A | 11/2018 |
| CN | 109044564 A | 12/2018 |
| CN | 109498216 A | 3/2019 |
| CN | 109498217 A | 3/2019 |
| DE | 4234127 C2 | 2/1996 |
| ES | 2660196 T3 | 3/2018 |
| IN | 212075 A1 | 11/2007 |
| IN | 6454CHENP2013 A | 10/2014 |
| JP | 055090013 A | 12/1993 |
| RU | 2141259 C1 | 11/1999 |
| RU | 2317020 C1 | 2/2008 |
| WO | 9724083 A1 | 7/1997 |
| WO | 9737618 A1 | 10/1997 |
| WO | 0182837 A2 | 11/2001 |
| WO | 02102237 A2 | 12/2002 |
| WO | 2004012583 A2 | 2/2004 |
| WO | 2004032796 A2 | 4/2004 |
| WO | 2006032054 A2 | 3/2006 |
| WO | 2006037073 A2 | 4/2006 |
| WO | 2006041877 A2 | 4/2006 |
| WO | 2006086434 A1 | 8/2006 |
| WO | 2006097931 A2 | 9/2006 |
| WO | 2007062054 A2 | 5/2007 |
| WO | 2007100268 A2 | 9/2007 |
| WO | 2008022077 A2 | 2/2008 |
| WO | 2008101113 A1 | 8/2008 |
| WO | 2009052427 A1 | 4/2009 |
| WO | 2009052528 A2 | 4/2009 |
| WO | 2009140298 A2 | 11/2009 |
| WO | 2009155561 A8 | 4/2011 |
| WO | 201113751 A9 | 1/2012 |
| WO | 2012020415 A2 | 2/2012 |
| WO | 2012035279 A1 | 3/2012 |
| WO | 2012037341 A1 | 3/2012 |
| WO | 2012106602 A2 | 8/2012 |
| WO | 2012142338 A2 | 10/2012 |
| WO | 2012166554 A2 | 12/2012 |
| WO | 2012177942 A2 | 12/2012 |
| WO | 2013003228 A1 | 1/2013 |
| WO | 2013028387 A2 | 2/2013 |
| WO | 2013075215 A1 | 5/2013 |
| WO | 2013082454 A1 | 6/2013 |
| WO | 2013114214 A2 | 8/2013 |
| WO | 2013175468 A2 | 11/2013 |
| WO | 2014087402 A1 | 6/2014 |
| WO | 2014093861 A1 | 6/2014 |
| WO | 2014189974 A1 | 11/2014 |
| WO | 2015048738 A1 | 4/2015 |
| WO | 2015061463 A1 | 4/2015 |
| WO | 2015125024 A2 | 8/2015 |
| WO | 2015191414 A2 | 12/2015 |
| WO | 2015191946 A1 | 12/2015 |
| WO | 2016079737 A2 | 5/2016 |
| WO | 201649453 A1 | 9/2016 |
| WO | 2017061956 A1 | 4/2017 |
| WO | 2017079153 A1 | 5/2017 |
| WO | 2017079698 A1 | 5/2017 |
| WO | 2017117560 A1 | 7/2017 |

(56) References Cited

FOREIGN PATENT DOCUMENTS

| | | |
|---|---|---|
| WO | 2017151566 A1 | 9/2017 |
| WO | 2018013856 A1 | 1/2018 |
| WO | 2017035002 A8 | 3/2018 |
| WO | 2018058157 A1 | 3/2018 |
| WO | 2018109329 A1 | 6/2018 |
| WO | 2018148839 A1 | 8/2018 |
| WO | 2018156856 A1 | 8/2018 |
| WO | 2018167388 A1 | 9/2018 |
| WO | 2018187753 A1 | 10/2018 |
| WO | 2018187805 A1 | 10/2018 |
| WO | 2018222086 A1 | 12/2018 |
| WO | 2019014643 A1 | 1/2019 |
| WO | 2019036810 A1 | 2/2019 |
| WO | 2019055154 A2 | 3/2019 |
| WO | 2019090249 A1 | 5/2019 |
| WO | 2019105073 A1 | 6/2019 |
| WO | 2019114448 A1 | 6/2019 |
| WO | 2019154847 A1 | 8/2019 |
| WO | 2019165213 A1 | 8/2019 |
| WO | 2019173385 A1 | 9/2019 |

\* cited by examiner

PERCUTANEOUS PAPILLARY MUSCLE RELOCATION

CROSS-REFERENCE TO RELATED APPLICATIONS

This application claims the benefit of priority under 35 U.S.C. § 119 to U.S. Provisional Application Ser. No. 62/675,118, filed May 22, 2018, the entirety of which is incorporated herein by reference.

TECHNICAL FIELD

The present disclosure pertains to medical devices and methods for using medical devices. More particularly, the present disclosure pertains to aspects of medical devices and/or means to deliver and release medical devices for percutaneously treating mitral regurgitation by relocating the papillary muscles of the heart.

BACKGROUND

A wide variety of intracorporeal medical devices have been developed for medical use, for example, surgical and/or intravascular use. Some of these devices include guidewires, catheters, medical device delivery systems (e.g., for stents, grafts, replacement valves, occlusive medical devices, etc.), and the like. These devices are manufactured by any one of a variety of different manufacturing methods and may be used according to any one of a variety of methods. There is an ongoing need to provide alternative medical devices as well as alternative methods for manufacturing and/or using medical devices.

SUMMARY

In a first aspect, a system for treating mitral regurgitation may comprise an outer sheath having a lumen extending to a distal end of the outer sheath, an intermediate sheath slidably disposed within the lumen of the outer sheath, the intermediate sheath having a lumen extending to a distal end of the intermediate sheath, and an inner sheath slidably disposed within the lumen of the intermediate sheath, wherein the inner sheath includes a first anchor disposed within a lumen of the inner sheath, the first anchor being configured to penetrate and secure to a first papillary muscle. The intermediate sheath may include a tissue grasping mechanism at the distal end of the intermediate sheath, the tissue grasping mechanism being configured to hold and stabilize the first papillary muscle for penetration and securement of the first anchor to the first papillary muscle.

In addition or alternatively, and in a second aspect, the tissue grasping mechanism includes a first prong and a second prong each attached to the distal end of the intermediate sheath. The first prong and the second prong may be configured to shift between a grasping configuration and an open configuration, the first prong and the second prong being biased toward the open configuration when unconstrained.

In addition or alternatively, and in a third aspect, in the open configuration, a gap between a distal end of the first prong and a distal end of the second prong is greater than an outer extent of the outer sheath.

In addition or alternatively, and in a fourth aspect, relative translation of the outer sheath and the tissue grasping mechanism toward each other urges the first prong and the second prong toward the grasping configuration.

In addition or alternatively, and in a fifth aspect, the intermediate sheath includes an actuator element extending proximally from the tissue grasping mechanism to an actuation position proximate a proximal end of the intermediate sheath.

In addition or alternatively, and in a sixth aspect, tension applied to the actuator element urges the first prong and the second prong toward the grasping configuration.

In addition or alternatively, and in a seventh aspect, the tissue grasping mechanism includes a curved member attached to the distal end of the intermediate sheath, the curved member being configured to extend around a majority of a circumference of the first papillary muscle.

In addition or alternatively, and in an eighth aspect, distal advancement of the inner sheath relative to the curved member until a distal end of the inner sheath is positioned against the first papillary muscle grasps the first papillary muscle to facilitate penetration of the first anchor into the first papillary muscle through the distal end of the inner sheath.

In addition or alternatively, and in a ninth aspect, the inner sheath includes a port extending through a side wall of the inner sheath proximate a distal end of the inner sheath, and at least one orientation marker positioned adjacent the port for determining an orientation of the port relative to the first papillary muscle. Distal advancement of the inner sheath relative to the curved member until the distal end of the inner sheath is positioned adjacent the first papillary muscle grasps the first papillary muscle to facilitate penetration of the first anchor into the first papillary muscle through the port at an angle generally perpendicular to a surface of the first papillary muscle being penetrated.

In addition or alternatively, and in a tenth aspect, the distal end of the inner sheath is a closed distal end.

In addition or alternatively, and in an eleventh aspect, a system for treating mitral regurgitation may comprise an outer sheath having a lumen extending to a distal end of the outer sheath, an intermediate sheath slidably disposed within the lumen of the outer sheath, the intermediate sheath having a lumen extending to a distal end of the intermediate sheath, an inner sheath slidably disposed within the lumen of the intermediate sheath, wherein the inner sheath includes a first anchor disposed within a lumen of the inner sheath, the first anchor being configured to penetrate and secure to a first papillary muscle, wherein the intermediate sheath includes a tissue grasping mechanism at the distal end of the intermediate sheath, the tissue grasping mechanism being configured to hold and stabilize the first papillary muscle for penetration and securement of the first anchor to the first papillary muscle, and a second anchor advanceable through the lumen of the inner sheath, the second anchor being configured to penetrate and secure to a second papillary muscle.

In addition or alternatively, and in a twelfth aspect, the first anchor and the second anchor are connectable to each other.

In addition or alternatively, and in a thirteenth aspect, the first anchor and the second anchor are configured to be connected to each other after deployment from the inner sheath.

In addition or alternatively, and in a fourteenth aspect, the first anchor and the second anchor are connected to each other by a tethering element.

In addition or alternatively, and in a fifteenth aspect, the tissue grasping mechanism is configured to hold and stabilize the second papillary muscle for penetration and securement of the second anchor to the second papillary muscle.

In addition or alternatively, and in a sixteenth aspect, a method for treating mitral regurgitation may comprise:

advancing a distal end of an outer sheath intravascularly to a left ventricle of a heart, the outer sheath having a lumen extending to the distal end of the outer sheath;

wherein an intermediate sheath is slidably disposed within the lumen of the outer sheath, the intermediate sheath having a lumen extending to a distal end of the intermediate sheath and a tissue grasping mechanism disposed at the distal end of the intermediate sheath; and wherein an inner sheath is slidably disposed within the lumen of the intermediate sheath;

grasping a first papillary muscle of the left ventricle using the tissue grasping mechanism, the tissue grasping mechanism being configured to hold and stabilize the first papillary muscle for penetration of a first anchor into the first papillary muscle from the inner sheath;

advancing the first anchor into the first papillary muscle from within a lumen of the inner sheath, the first anchor being configured to penetrate and secure to the first papillary muscle of the left ventricle;

grasping a second papillary muscle of the left ventricle using the tissue grasping mechanism at the distal end of the intermediate sheath, the tissue grasping mechanism being configured to hold and stabilize the second papillary muscle for penetration of a second anchor into the second papillary muscle from the inner sheath;

advancing the second anchor into the second papillary muscle from within the lumen of the inner sheath, the second anchor being configured to penetrate and secure to the second papillary muscle of the left ventricle; and releasing the second papillary muscle from the tissue grasping mechanism, wherein a tethering element extends from the first anchor to the second anchor to connect and reposition the first papillary muscle relative to the second papillary muscle.

In addition or alternatively, and in a seventeenth aspect, the first anchor and the second anchor each include an eyelet, and the tethering element extends between the eyelet of the first anchor and the eyelet of the second anchor.

In addition or alternatively, and in an eighteenth aspect, at least a portion of each of the first anchor and the second anchor is configured to extend transversely relative to the tethering element when unconstrained by the inner sheath.

In addition or alternatively, and in a nineteenth aspect, at least one of the first anchor and the second anchor includes a plurality of anchor legs extending from the eyelet to free ends, wherein the plurality of anchor legs is configured to shift from a delivery configuration when constrained by the inner sheath to a deployed configuration when unconstrained by the inner sheath. In the delivery configuration, the free ends of the plurality of anchor legs may point in a distal direction, and in the deployed configuration the free ends of the plurality of anchor legs may point in a proximal direction.

In addition or alternatively, and in a twentieth aspect, the method further includes translating the first papillary muscle closer to the second papillary muscle by tensioning the tethering element between the first anchor and the second anchor.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
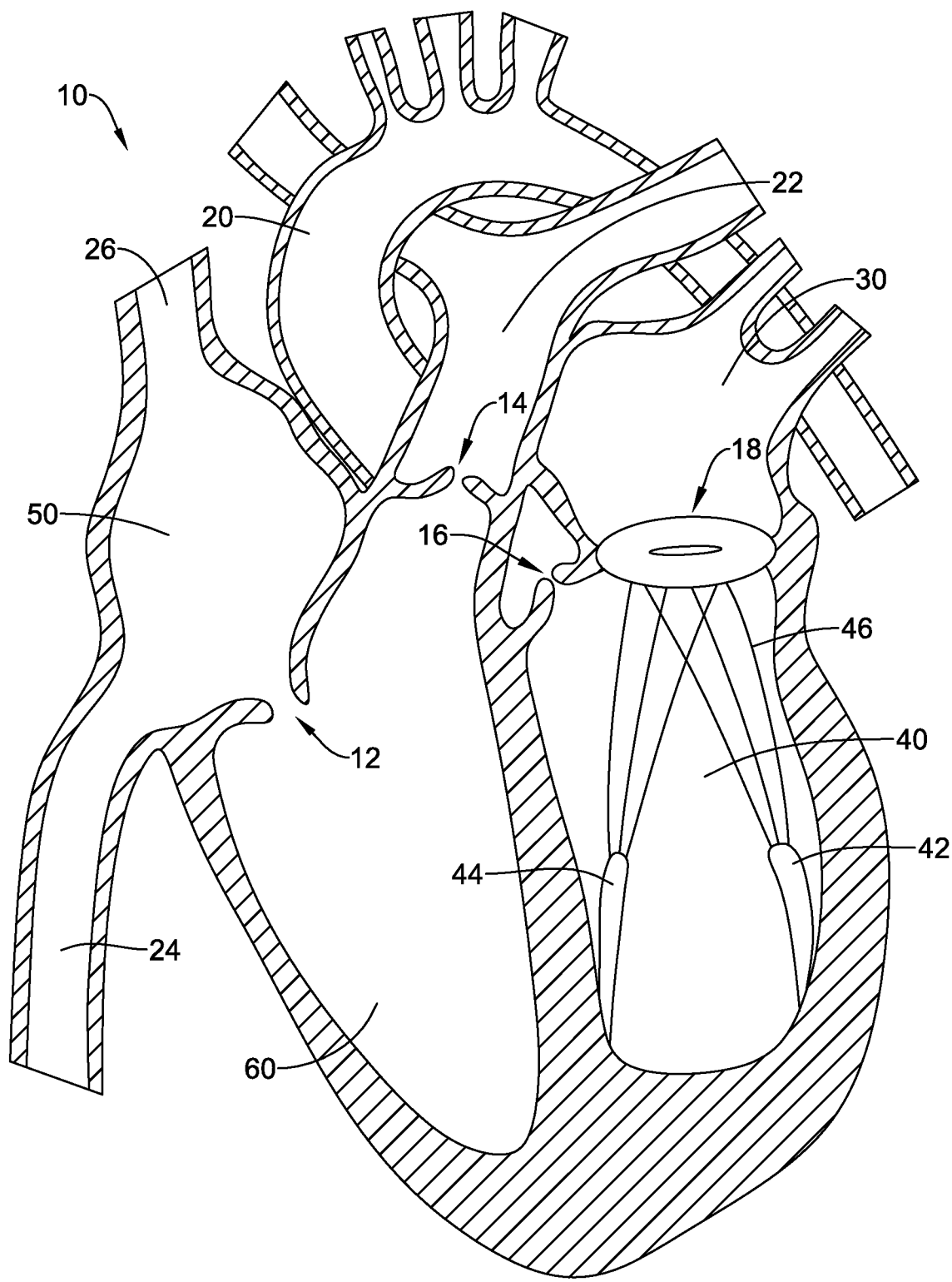
FIG. 1 is a partial cut-away view of an example heart having a "distended" left ventricle and/or experiencing mitral regurgitation.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

The terms "extent" and/or "maximum extent" may be understood to mean a greatest measurement of a stated or identified dimension, while the term "minimum extent" may be understood to mean a smallest measurement of a stated or identified dimension. For example, "outer extent" may be understood to mean a maximum outer dimension, "radial extent" may be understood to mean a maximum radial dimension, "longitudinal extent" may be understood to mean a maximum longitudinal dimension, etc. Each instance of an "extent" may be different (e.g., axial, longitudinal, lateral, radial, circumferential, etc.) and will be apparent to the skilled person from the context of the individual usage. Generally, an "extent" or "maximum extent" may be considered a greatest possible dimension measured according to the intended usage. Alternatively, a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Diseases and/or medical conditions that impact the cardiovascular system are prevalent throughout the world. Some mammalian hearts (e.g., human, etc.) include four heart valves: a tricuspid valve 12, a pulmonary valve 14, an aortic valve 16, and a mitral valve 18, as seen in an example heart 10 illustrated in FIG. 1. The purpose of the heart valves is to control blood flow into the heart 10 from the inferior vena cava 24 and/or the superior vena cava 26, through the heart 10, and out of the heart 10 into the major blood vessels connected to the heart 10, such as the aorta 20, the pulmonary artery 22, for example. Each heart valve may have a plurality of valve leaflets configured to shift between an open configuration permitting fluid flow through the heart valve in an antegrade direction, and a closed configuration wherein free edges of the valve leaflets coapt to substantially prevent fluid flow through the heart valve in a retrograde direction. The heart 10 may also include a left atrium 30, a left ventricle 40, a right atrium 50, and a right ventricle 60. The left ventricle 40 may include a first papillary muscle 42 attached to and/or extending from a wall of the left ventricle 40, a second papillary muscle 44 attached to and/or extending from the wall of the left ventricle 40, and a plurality of chordae 46 connecting the first papillary muscle 42 and the second papillary muscle 44 to the leaflets of the mitral valve 18. In a normally functioning heart valve, blood is permitted to pass or flow downstream through the heart valve (e.g., from an atrium to a ventricle, from a ventricle to an artery, etc.) when the heart valve is open (e.g., during diastole), and when the heart valve is closed (e.g., during systole), blood is prevented from passing or flowing back upstream through the heart valve (e.g., from a ventricle to an atrium, etc.).

In some instances, when regurgitation (e.g., mitral regurgitation) occurs, a heart valve (e.g., the mitral valve 18) fails to open and/or close properly such that blood is permitted to pass or flow back upstream through the heart valve (e.g., from a ventricle to an atrium, etc.). In some cases, the defective heart valve may have leaflets that may not close, or may not be capable of closing, completely. In some instances, secondary or functional mitral regurgitation may be a secondary effect of left ventricular dysfunction, where left ventricular dilatation and/or distension caused by ischemic or idiopathic cardiomyopathy, for example, results in annular dilatation and/or distension of the left ventricle 40 and papillary muscle displacement with subsequent leaflet tethering and insufficient coaptation of the mitral leaflets during systole, as seen in FIG. 1 for example. As the left ventricle 40 dilates and/or distends outward, the first and second papillary muscles 42/44 are displaced outward and/or away from the mitral valve 18. Displacement of the first and second papillary muscles 42/44 adds tension to the chordae 46 connecting the first and second papillary muscles 42/44 to the mitral valve leaflets, and/or changes the tension on the chordae 46 with respect to a directional vector of the tension, resulting in leaflet tethering and/or insufficient coaptation of the mitral leaflets during systole.

Disclosed herein are apparatus, medical devices, and/or methods that may be used to diagnose, treat, and/or repair a portion of the cardiovascular system. One possible remedy is an annular reduction procedure that may be performed to reduce an overall extent of the defective heart valve to bring the heart valve leaflets closer together. In some procedures, the annular reduction procedure may be performed in conjunction with a sub-valvular repair technique involving relocation of the papillary muscles to reduce leaflet tethering, thereby permitting the heart valve leaflets to more properly close the defective heart valve the passage of blood. The disclosed mitral regurgitation treatment method(s) and associated medical device(s) may be performed/used percutaneously via minimally-invasive intravascular techniques, or in an alternative method, using open-heart surgical methods. The device(s) and method(s) disclosed herein may also provide a number of additional desirable features and/or benefits as described in more detail below. For the purpose of this disclosure, the discussion below is directed toward repairing the mitral valve 18 and will be so described in the interest of brevity. This, however, is not intended to be limiting as the skilled person will recognize that the following discussion may also apply to the aortic valve 16 or another heart valve (e.g., the tricuspid valve 12, the pulmonary valve 14, etc.) with no or minimal changes to the structure and/or scope of the disclosure.

A mitral regurgitation treatment system may reposition the first papillary muscle 42 and/or the second papillary muscle 44 relative to each other, relative to the wall of the left ventricle 40, and/or relative to the mitral valve 18 and/or the annulus of the mitral valve 18. In some embodiments, the mitral regurgitation treatment system may pull the first papillary muscle 42 closer to the second papillary muscle 44. In some embodiments, pulling the first papillary muscle 42 closer to the second papillary muscle 44 may also relocate the wall of the left ventricle 40, thereby reducing and/or eliminating the magnitude of dilatation and/or distension of the left ventricle 40, which also serves to reduce tension on the chordae 46, reduce leaflet tethering, and improves coaptation of the mitral leaflets during systole. In some embodiments, pulling the first papillary muscle 42 closer to the second papillary muscle 44 may have limited effect upon the wall of the left ventricle 40 but may still reduce tension on the chordae 46, reduce leaflet tethering, and improves coaptation of the mitral leaflets during systole due to relocation of the first papillary muscle 42 and the second papillary muscle 44 closer to each other and/or the mitral valve 18.

Figure 2:
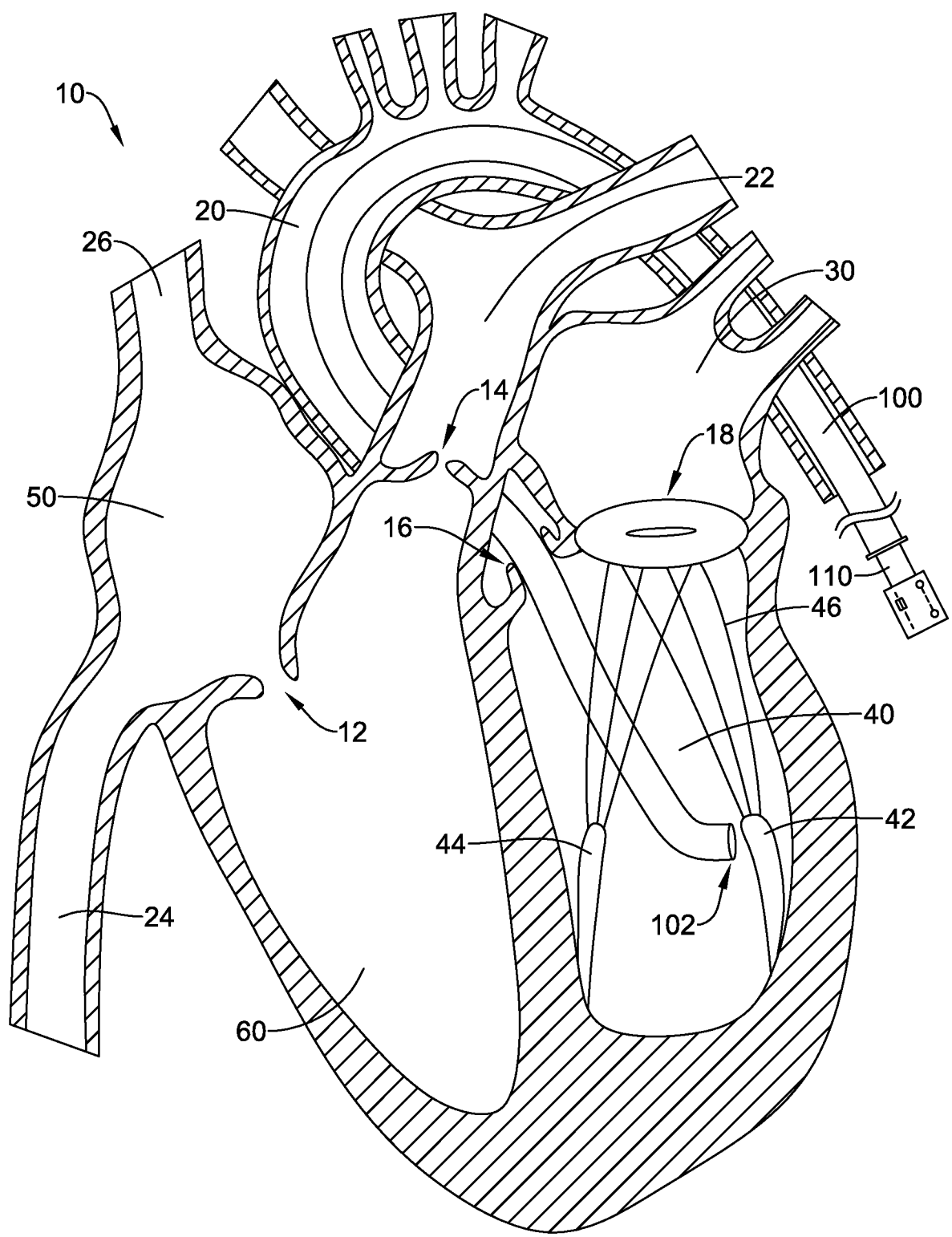
FIG. 2 illustrates aspects of an example method of treating mitral regurgitation.

FIG. 2 illustrates selected aspects of an example method of treating mitral regurgitation. In at least some embodiments, the method may include advancing a distal end 102 of an outer sheath 100 of a mitral regurgitation treatment system intravascularly to the left ventricle 40 of the heart 10. In some embodiments, the outer sheath 100 of the mitral regurgitation treatment system may be inserted through a femoral artery and advanced in a retrograde direction (e.g., upstream) through the aorta 20 and the aortic valve 16 into the left ventricle 40 of the heart 10. Alternative percutaneous approaches, including but not limited to transseptal access, as well as additional alternative methods including but not limited to an apical approach, are also contemplated.

The outer sheath 100 may have a lumen extending to the distal end 102 of the outer sheath 100. In some embodiments, the lumen may extend completely through the outer sheath 100 to a proximal end of the outer sheath 100. Alternatively, in some embodiments, a proximal end of the lumen may exit the outer sheath 100 distal of the proximal end of the outer sheath 100. In some embodiments, the distal end 102 and/or a distal portion of the outer sheath 100 may be steerable to facilitate navigation and treatment procedures. The distal end 102 and/or the distal portion of the outer sheath 100 may be steerable to direct an opening from the lumen toward the first papillary muscle 42 and/or the second papillary muscle 44, as discussed herein. The proximal end of the outer sheath 100 may be disposed and/or be configured to be manipulated by a user outside of a patient's anatomy.

Figure 3:
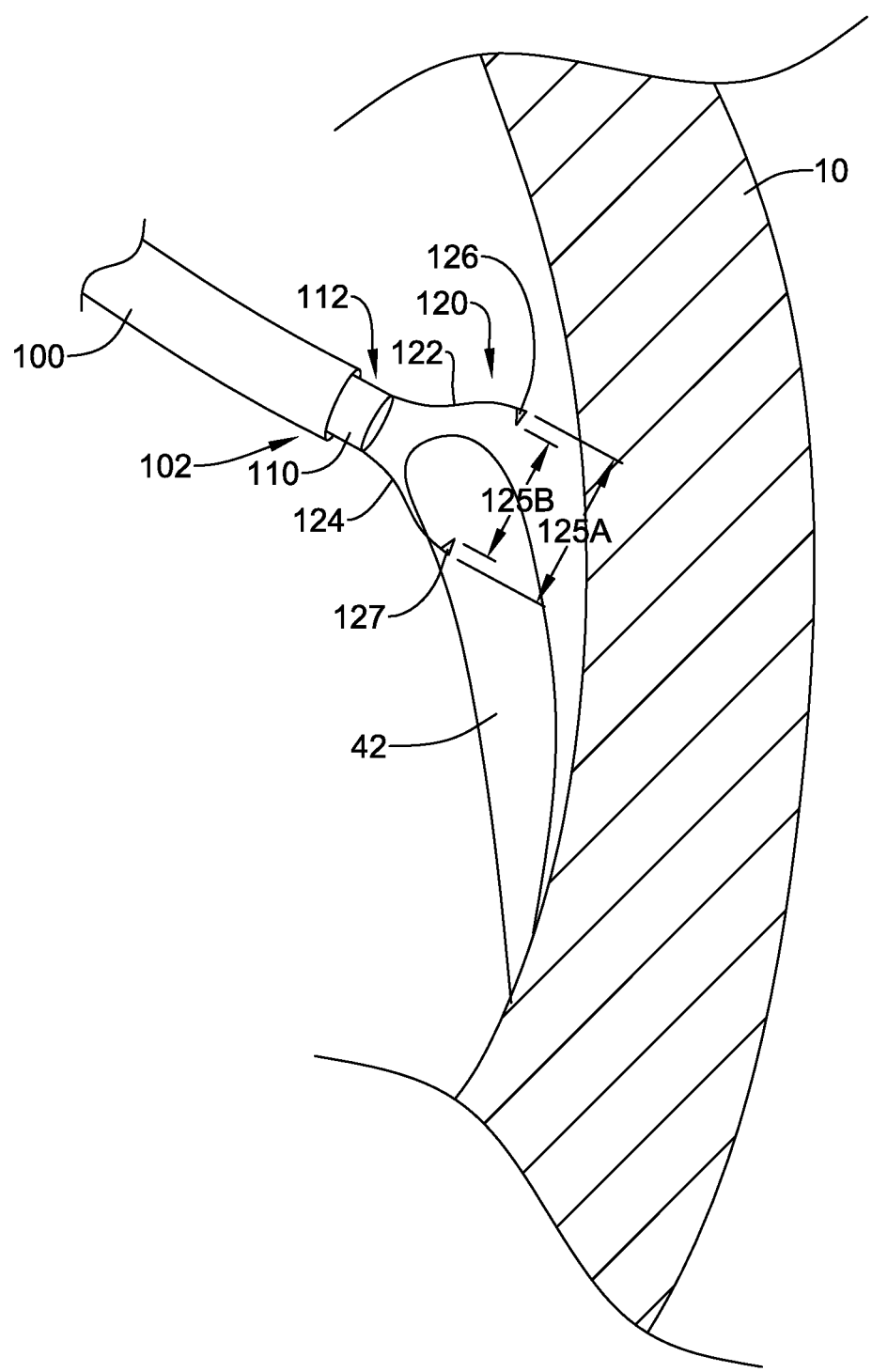
FIGS. 3-4 illustrate an example configuration of a mitral regurgitation treatment system.

In some embodiments, the mitral regurgitation treatment system may include an intermediate sheath 110 slidably disposed within the lumen of the outer sheath 100. The intermediate sheath 110, a proximal portion of which may be seen in FIG. 2 adjacent the proximal end of the outer sheath 100, may have a lumen extending to a distal end 112 of the intermediate sheath 110 and a tissue grasping mechanism 120 disposed at the distal end 112 of the intermediate sheath 110, as seen in FIG. 3 for example. Additional and/or alternative forms for the tissue grasping mechanism 120 may be seen in FIGS. 5 (e.g., tissue grasping mechanism 220), 7 (e.g., tissue grasping mechanism 320), 12 (e.g., tissue grasping mechanism 290), and 13 (e.g., tissue grasping mechanism 294), and will be discussed in more detail herein. It should be understood that while aspects of the tissue grasping mechanism(s) are illustrated with respect to the first papillary muscle 42 in the interest of brevity, any and/or all aspects of the tissue grasping mechanism(s) 120/220/320/290/294 may apply equally with respect to the second papillary muscle 44 and/or any procedures or method steps occurring with respect thereto.

In some embodiments, the tissue grasping mechanism 120 may include a first prong 122 and a second prong 124 each fixedly attached to the distal end 112 of the intermediate sheath 110, as seen in FIG. 3 for example. In some embodiments, the first prong 122 and the second prong 124 may be integrally formed with the intermediate sheath 110. In some embodiments, the first prong 122 and the second prong 124 may each be at least partially embedded within a wall of the intermediate sheath 110. In some embodiments, a proximal end of each of the first prong 122 and the second prong 124 may be attached, affixed, and/or secured to an outer surface of the intermediate sheath 110. Various known means of attachment may be used, including but not limited to, adhesives, shrink wrap, welding, mechanical attachment, etc. The first prong 122 and the second prong 124 of the tissue grasping mechanism 120 may be configured to shift between a grasping configuration, shown in FIG. 4 for example, and an open configuration (e.g., FIG. 3). The first prong 122 and the second prong 124 of the tissue grasping mechanism 120 may be biased toward the open configuration when unconstrained, such as when disposed outside of the outer sheath 100, for example. In at least some embodiments, the first prong 122 and the second prong 124 may be self-biased toward the open configuration when unconstrained.

In the open configuration, a gap 125A between a distal end of the first prong 122 and a distal end of the second prong 124, and more particularly a gap 125B between a first barb 126 on the first prong 122 extending toward the second prong 124 and a second barb 127 on the second prong 124 extending toward the first prong 122, is greater than an outer extent of the outer sheath 100 measured across the gap 125A/125B and/or normal to a longitudinal axis of the outer sheath 100. In the open configuration, the gap 125A/125B may permit the first prong 122 and the second prong 124 of the to fit around and/or encompass at least a portion of the first papillary muscle 42 and/or the second papillary muscle 44, as seen in FIG. 3.

Figure 4:
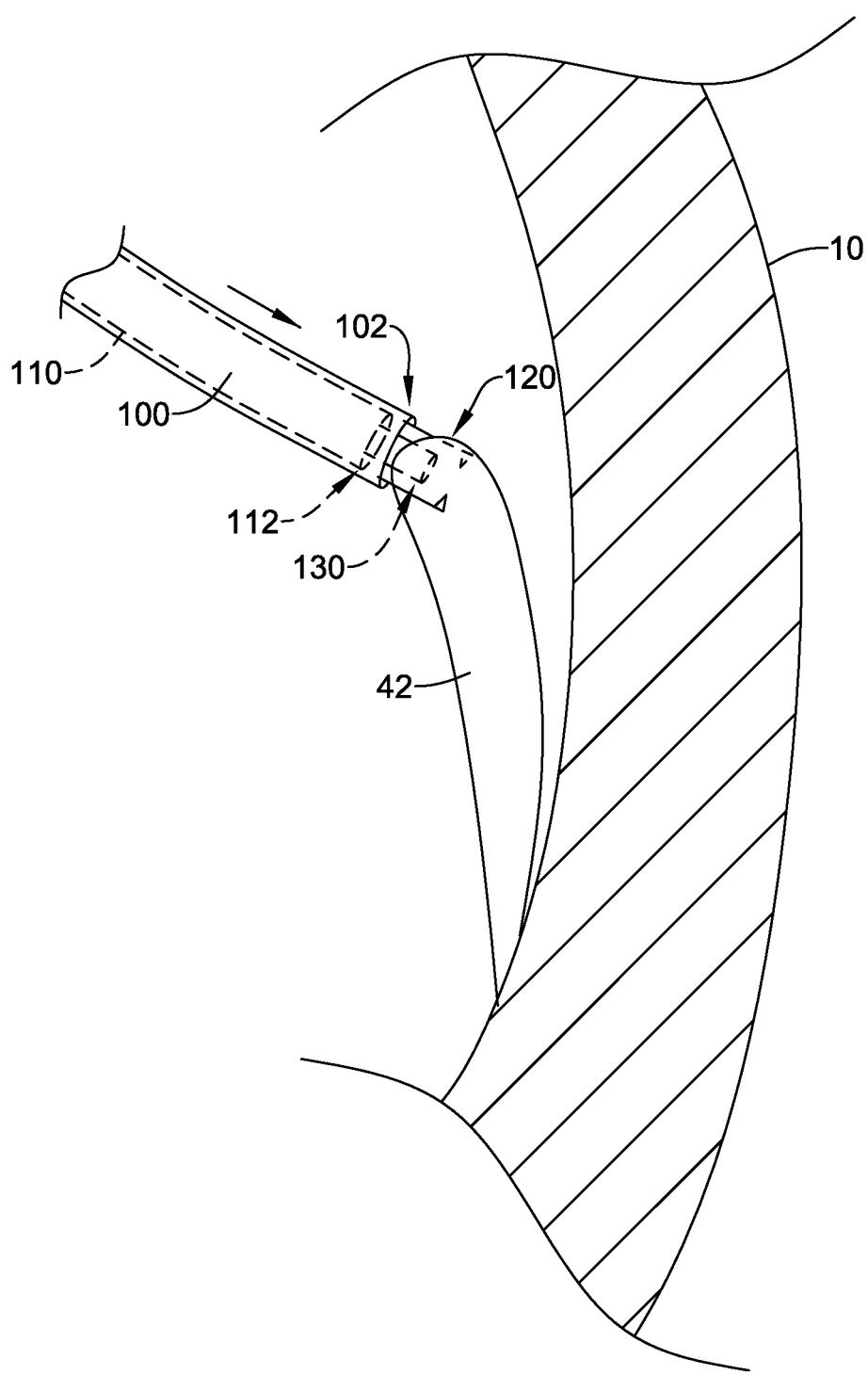

In the grasping configuration, the tissue grasping mechanism 120 may be configured to hold and stabilize the first papillary muscle 42 and/or the second papillary muscle 44, as seen in FIG. 4. In order to achieve the grasping configuration, the outer sheath 100 may be advanced distally while the intermediate sheath 110 and/or the tissue grasping mechanism 120 is maintained in a static position, and/or the intermediate sheath 110 and/or the tissue grasping mechanism 120 may be retracted proximally while the outer sheath 100 is maintained in a static position, such that relative translation between the outer sheath 100 and the intermediate sheath 110 and/or the tissue grasping mechanism 120 moves the distal end 102 of the outer sheath 100 over the first prong 122 and the second prong 124 of the tissue grasping mechanism 120, thereby urging the first prong 122 and the second prong 124 towards each other and/or the grasping configuration. In the grasping configuration, the first papillary muscle 42 and/or the second papillary muscle 44 may be pinched, squeezed, and/or otherwise held between the first prong 122 and the second prong 124 of the tissue grasping mechanism 120. An anchor may then be inserted into and/or through the papillary muscle from an inner sheath 130, as described herein.

Figure 5:
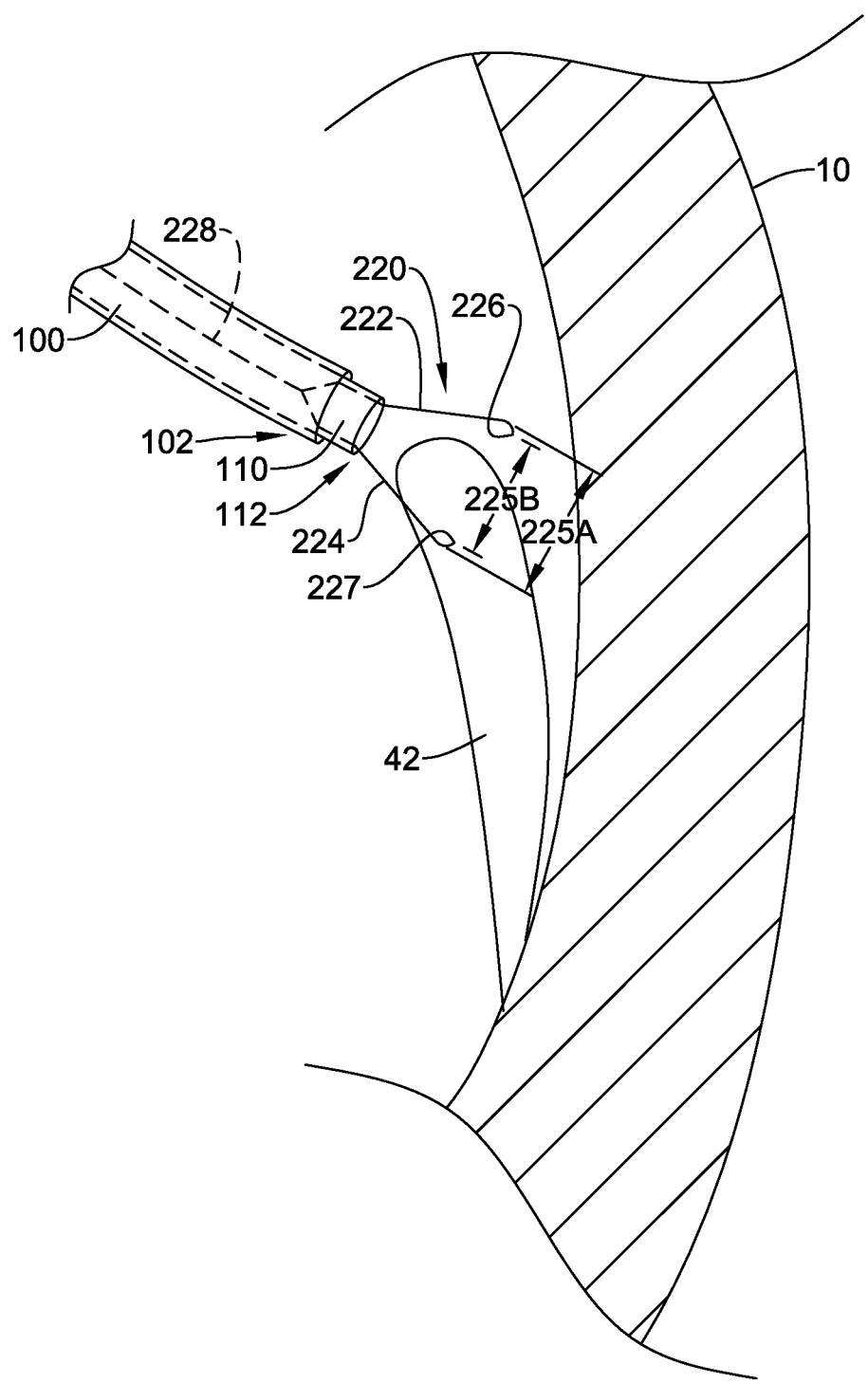
FIGS. 5-6 illustrate an example configuration of a mitral regurgitation treatment system.
Figure 6:
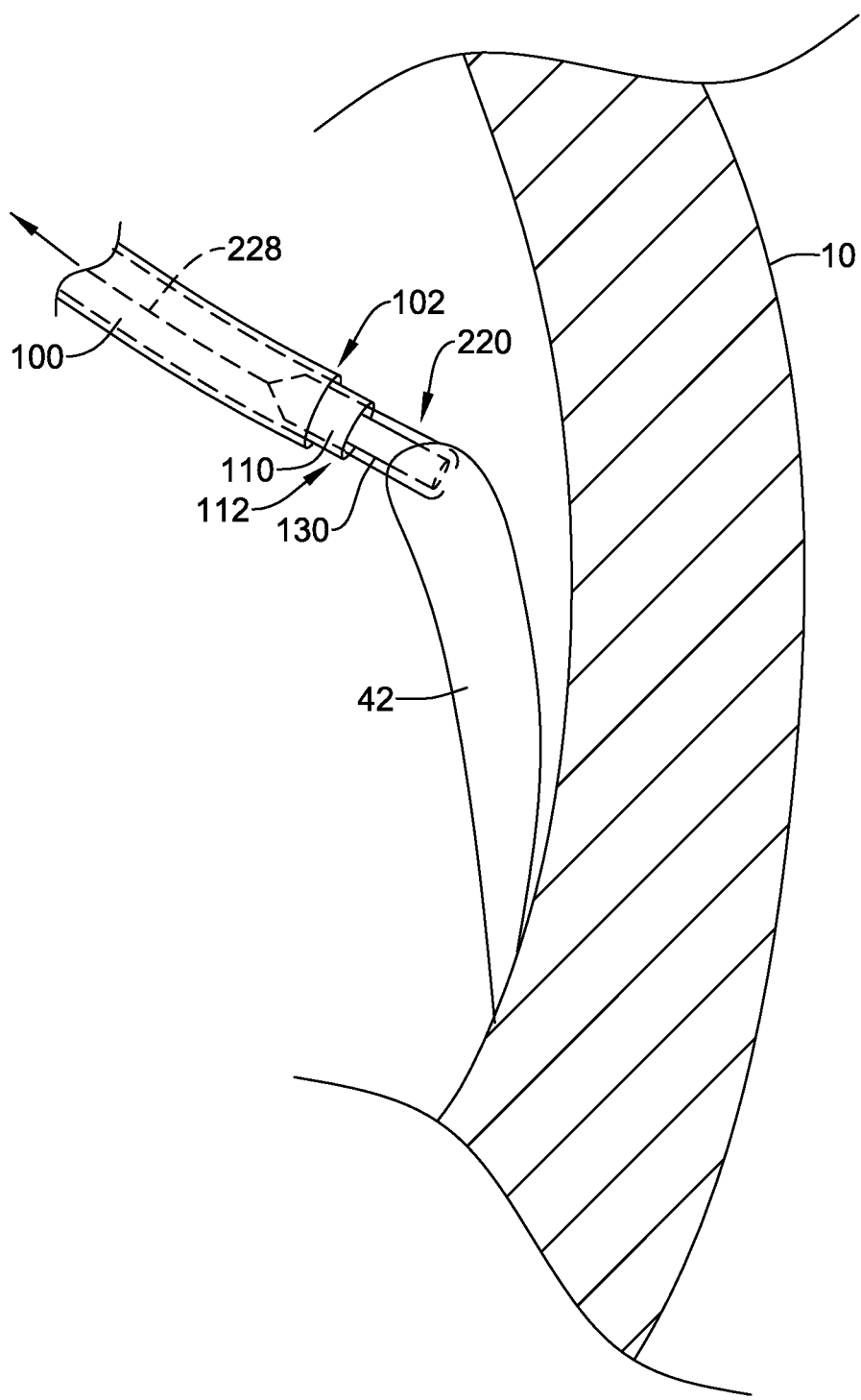

FIGS. 5 and 6 illustrate an alternative configuration of a tissue grasping mechanism 220 disposed at the distal end 112 of the intermediate sheath 110. In some embodiments, the tissue grasping mechanism 220 may include a first prong 222 and a second prong 224 configured to shift between a grasping configuration, shown in FIG. 6 for example, and an open configuration (e.g., FIG. 5). The first prong 222 and the second prong 224 of the tissue grasping mechanism 220 may be biased toward the open configuration when unconstrained, such as when disposed outside of the outer sheath 100, for example. In at least some embodiments, the first prong 222 and the second prong 224 may be self-biased toward the open configuration when unconstrained.

In the open configuration, a gap 225A between a distal end of the first prong 222 and a distal end of the second prong 224, and more particularly a gap 225B between a first barb 226 on the first prong 222 extending toward the second prong 224 and a second barb 227 on the second prong 224 extending toward the first prong 222, is greater than an outer extent of the outer sheath 100 measured across the gap 225A/225B and/or normal to a longitudinal axis of the outer sheath 100. In the open configuration, the gap 225A/225B may permit the first prong 222 and the second prong 224 of the to fit around and/or encompass at least a portion of the first papillary muscle 42 and/or the second papillary muscle 44, as seen in FIG. 5.

In the grasping configuration, the tissue grasping mechanism 220 may be configured to hold and stabilize the first papillary muscle 42 and/or the second papillary muscle 44, as seen in FIG. 6. In order to achieve the grasping configuration, the outer sheath 100 may be maintained in a static position, and an actuator element 228 extending proximally from the tissue grasping mechanism 120 to an actuation position (e.g., FIG. 2) proximate a proximal end of the intermediate sheath 110 may be retracted proximally, such that relative translation between the outer sheath 100 and actuator element 228 and/or the tissue grasping mechanism 220 urges the first prong 222 and the second prong 224 of the tissue grasping mechanism 220 towards each other and/or the grasping configuration. For example, tension applied to the actuator element 228 may urge the first prong 222 and the second prong 224 towards each other and/or the grasping configuration by translating the tissue grasping mechanism 220 into the distal end 112 of the intermediate sheath 110. Alternatively, the first prong 222 and the second prong 224 may be hingedly connected proximate a proximal end of the first prong 222 and the second prong 224, and the actuator element 228 may be connected to each of the first prong 222 and the second prong 224 distal of the hinged connection such that tension applied to the actuator element 228 may urge the first prong 222 and the second prong 224 towards each other and/or the grasping configuration by causing the first prong 222 and the second prong 224 to pivot towards each other and/or toward the grasping configuration at the hinged connection. In the grasping configuration, the first papillary muscle 42 and/or the second papillary muscle 44 may be pinched, squeezed, and/or otherwise held between the first prong 222 and the second prong 224 of the tissue grasping mechanism 220. An anchor may then be inserted into and/or through the papillary muscle from an inner sheath, as described herein.

Figure 7:
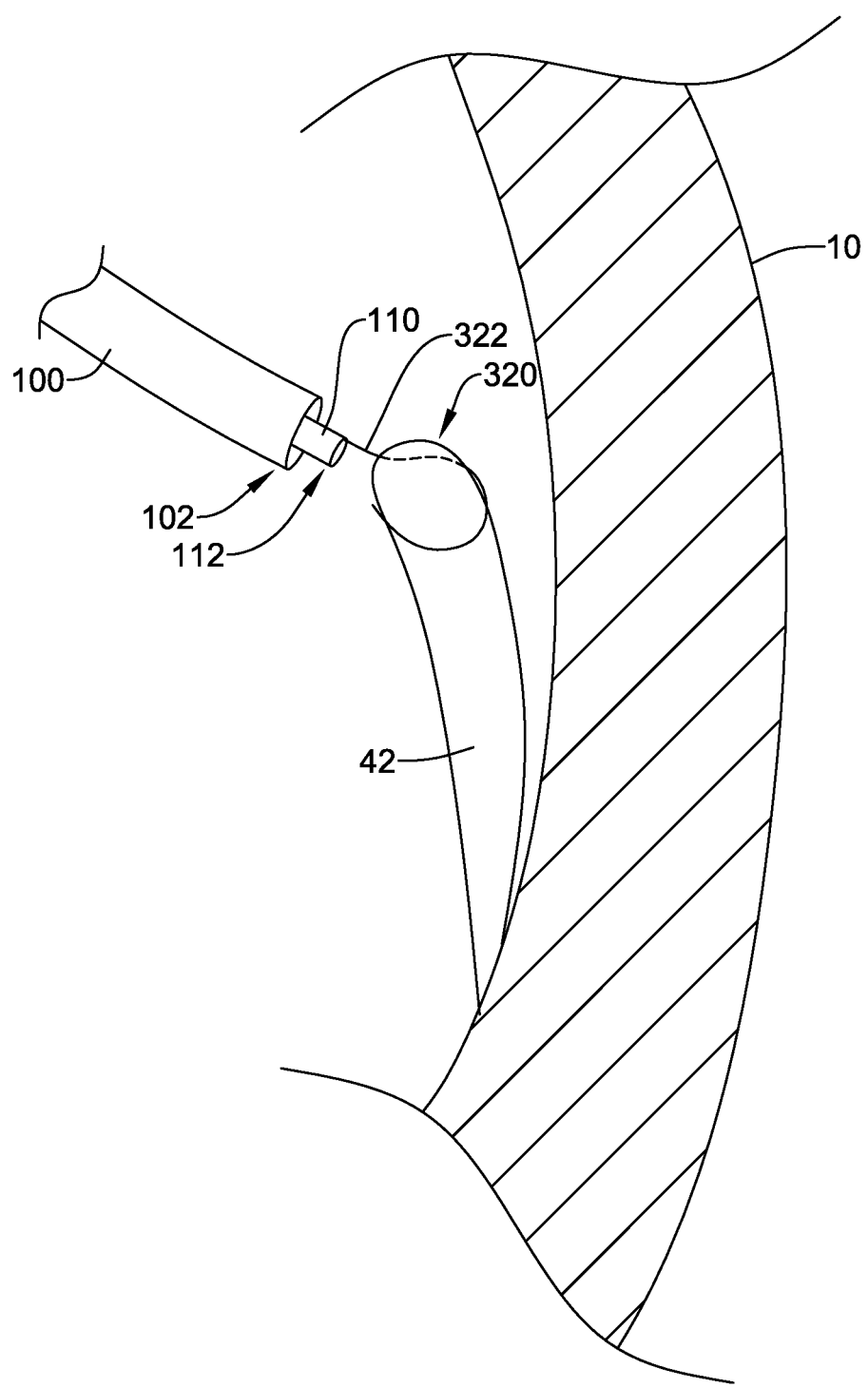
FIGS. 7-8 illustrate an example configuration of a mitral regurgitation treatment system.

In another alternative configuration, the intermediate sheath 110 may include a tissue grasping mechanism 320 at the distal end 112 of the intermediate sheath 110. The tissue grasping mechanism 320 may include a curved member 322 fixedly attached to the distal end 112 of the intermediate sheath 110, as seen in FIG. 7 for example. In some embodiments, the curved member 322 may be integrally formed with the intermediate sheath 110. In some embodiments, the curved member 322 may be at least partially embedded within a wall of the intermediate sheath 110. In some embodiments, a proximal end of the curved member 322 may be attached, affixed, and/or secured to an outer surface of the intermediate sheath 110. Various known means of attachment may be used, including but not limited to, adhesives, shrink wrap, welding, mechanical attachment, etc.

The curved member 322 may be configured to shift between a delivery configuration, wherein the curved member 322 is constrained by and straightened by the outer sheath 100, and a curved configuration, wherein when the curved member 322 is unconstrained, the curved member 322 is biased towards the curved configuration and/or shape, as illustrated in FIG. 7 for example. In at least some embodiments, the curved member 322 may be self-biased towards the curved configuration. For example, in some embodiments, the curved member 322 may be formed from a shape memory alloy and/or may be heat set to the curved configuration and/or shape. As the intermediate sheath 110 is advanced through and/or out of the distal end 102 of the outer sheath 100, the curved member 322 may be deployed and allowed/permitted to shift towards the curved configuration. During use, the intermediate sheath 110 and/or the curved member 322 may be maneuvered within the left ventricle 40 to position the curved member 322 around the first papillary muscle 42 and/or the second papillary muscle 44, using a suitable imaging technique (e.g., ultrasound, etc.). The curved member 322 may be adapted and/or configured to extend around a majority of a circumference of the first papillary muscle 42 and/or the second papillary muscle 44 in the curved configuration.

Figure 8:
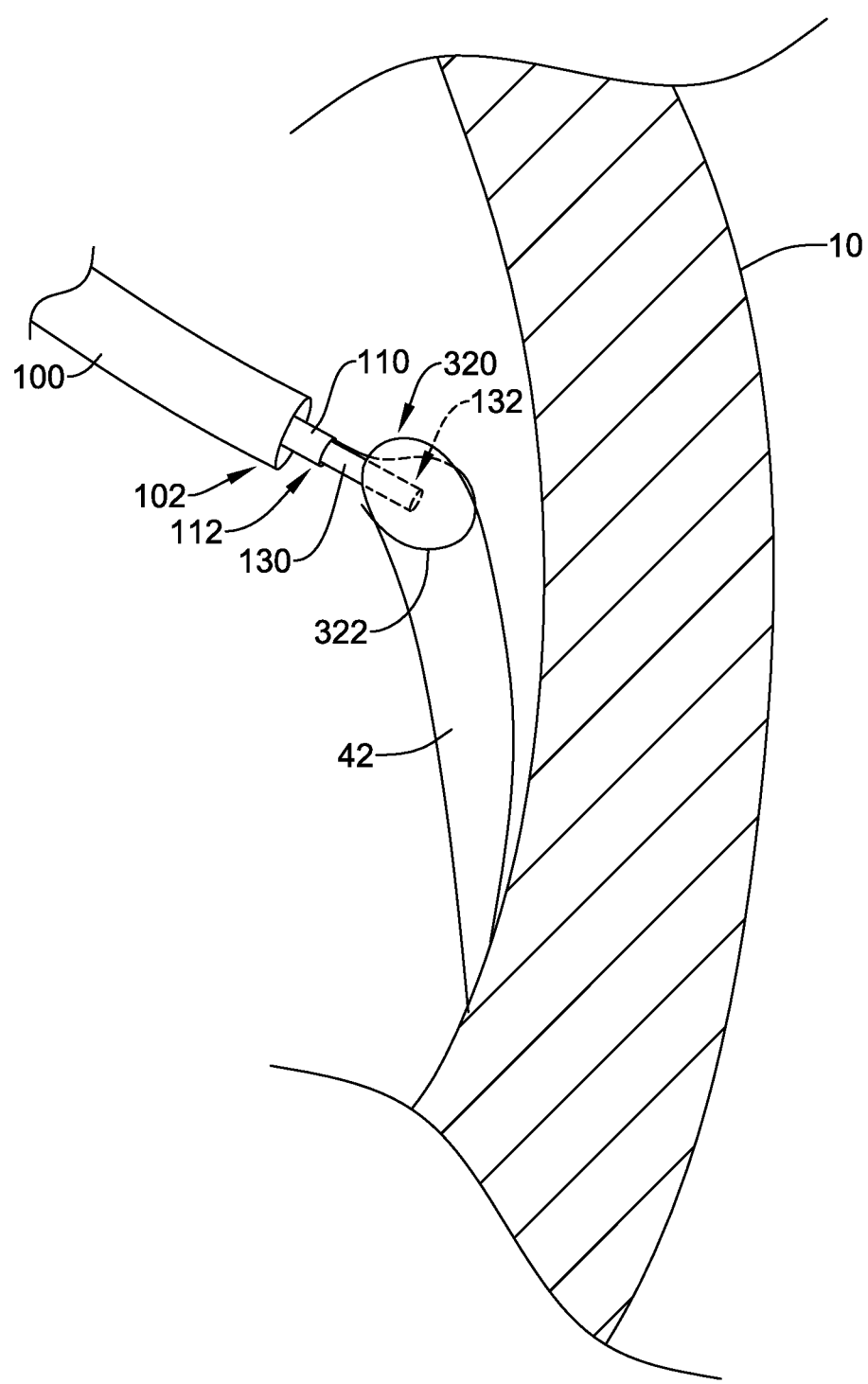

In order to fully secure the first papillary muscle 42 and/or the second papillary muscle 44, an inner sheath 130 slidably disposed within the lumen of the intermediate sheath 110 may be extended out of the distal end 112 of the intermediate sheath 110 and into contact with an outer surface of the first papillary muscle 42 and/or the second papillary muscle 44, as seen in FIG. 8 for example. The first papillary muscle 42 and/or the second papillary muscle 44 may be pinched, squeezed, and/or otherwise held between inner sheath 130 and the curved member 322.

In some embodiments, distal advancement of the inner sheath 130 relative to the curved member 322 and/or the intermediate sheath 110 until a distal end 132 of the inner sheath 130 is positioned against the outer surface of the first papillary muscle 42 and/or the second papillary muscle 44 may grasp the first papillary muscle 42 and/or the second papillary muscle 44 to facilitate penetration of an anchor into the first papillary muscle 42 and/or the second papillary muscle 44 through an opening at the distal end 132 of the inner sheath 130, as discussed herein. A central longitudinal axis of the inner sheath 130 and/or the opening at the distal end 132 of the inner sheath 130 may be oriented substantially perpendicular to the outer surface of the first papillary muscle 42 and/or the second papillary muscle 44.

Figure 9:
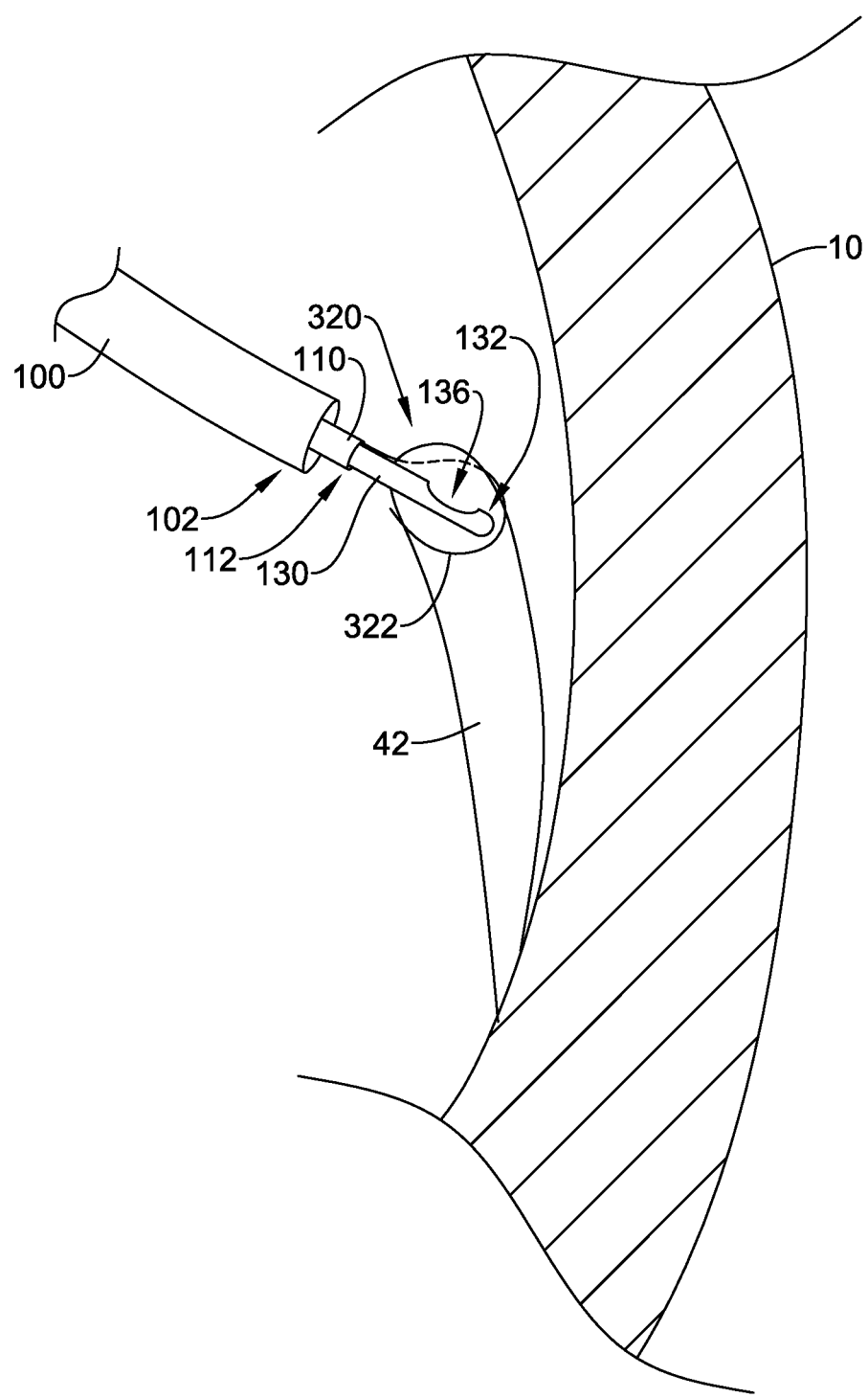
FIG. 9 illustrates an alternative configuration of the mitral regurgitation treatment system of FIGS. 7-8.

In an alternative configuration, the inner sheath 130 may include a port 136 extending through a side wall of the inner sheath 130 proximate the distal end 132 of the inner sheath 130, as seen in FIG. 9 for example, instead of and/or in addition to the opening at the distal end 132 of the inner sheath 130. In some embodiments, the distal end 132 of the inner sheath 130 may be a closed distal end. In some embodiments, distal advancement of the inner sheath 130 relative to the curved member 322 and/or the intermediate sheath 110 until the distal end 132 of the inner sheath 130 is positioned adjacent the first papillary muscle 42 and/or the second papillary muscle 44 may grasp the first papillary muscle 42 and/or the second papillary muscle 44 to facilitate penetration of an anchor into the first papillary muscle 42 and/or the second papillary muscle 44 through the port 136 at an angle generally perpendicular to a surface of the first papillary muscle 42 and/or the second papillary muscle 44 being penetrated, as discussed herein. In at least some embodiments, the central longitudinal axis of the inner sheath 130 may be oriented substantially parallel to the outer surface of the first papillary muscle 42 and/or the second papillary muscle 44 being penetrated such that the port 136 generally abuts the outer surface of the first papillary muscle 42 and/or the second papillary muscle 44 being penetrated.

Figure 10:
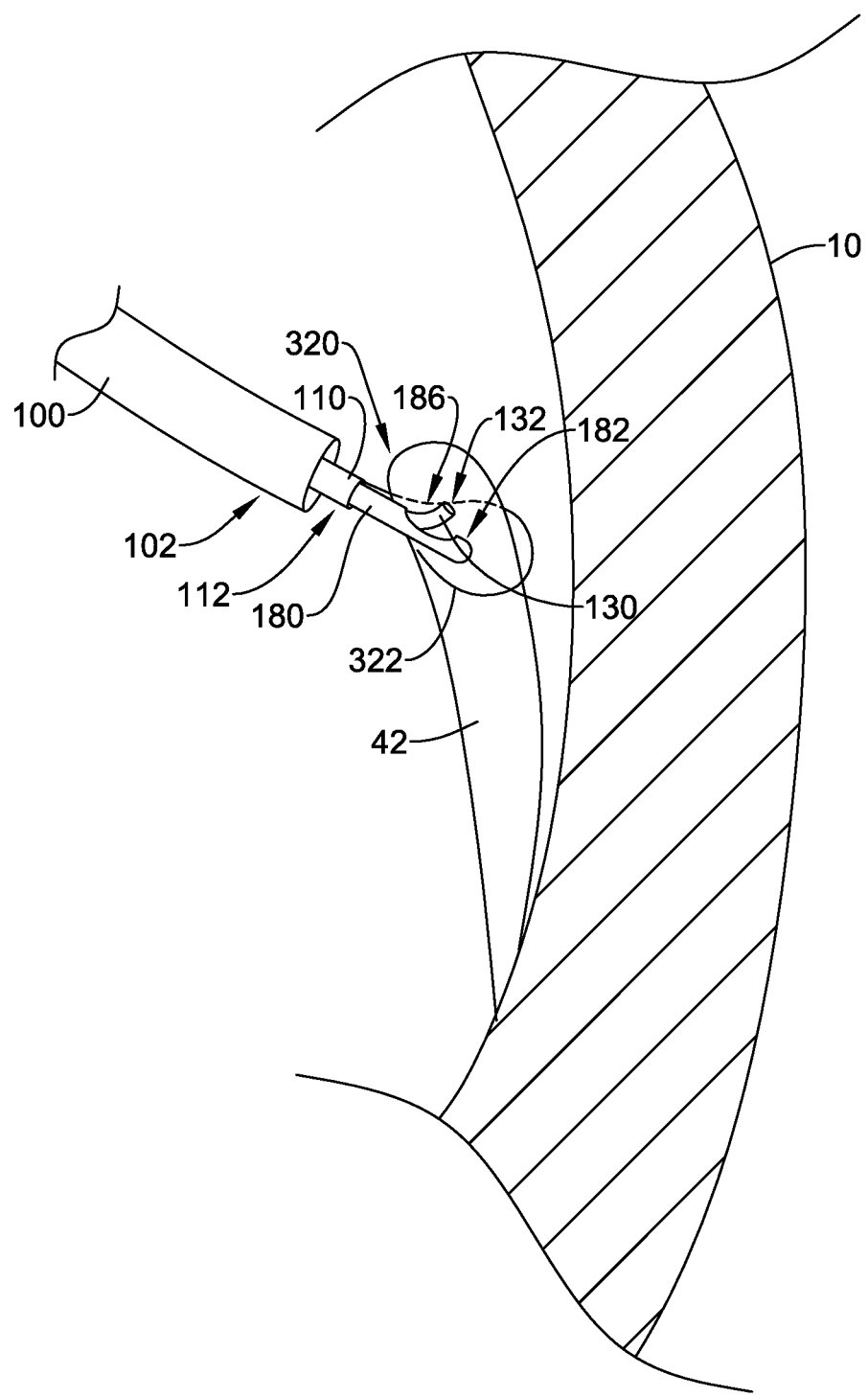
FIG. 10 illustrates an example configuration of a mitral regurgitation treatment system.

In another example configuration of the mitral regurgitation treatment system, a positioning sheath 180 may be slidably disposed within the lumen of the intermediate sheath 110. The positioning sheath 180 may include a distal end 182 and a port 186 extending through a side wall of the positioning sheath 180 proximate the distal end 182 of the positioning sheath 180, as seen in FIG. 10 for example. In at least some embodiments, the distal end 182 of the positioning sheath 180 may be a closed distal end. The inner sheath 130 may be slidably disposed within a lumen of the positioning sheath 180. In at least some embodiments, the lumen of the positioning sheath 180 and/or the port 186 of the positioning sheath 180 may be configured to direct the distal end 132 of the inner sheath 130 toward and/or into contact with the first papillary muscle 42 and/or the second papillary muscle 44 upon advancement of the inner sheath 130 relative to the positioning sheath 180, the intermediate sheath 110, and/or the curved member 322. In some embodiments, the positioning sheath 180 may be configured to cooperate with the inner sheath 130 to facilitate penetration of an anchor into the first papillary muscle 42 and/or the second papillary muscle 44 through an opening at the distal end 132 of the inner sheath 130 at an angle generally perpendicular to a surface of the first papillary muscle 42 and/or the second papillary muscle 44 being penetrated, as discussed herein. In at least some embodiments, a central longitudinal axis of the positioning sheath 180 may be oriented substantially parallel to the outer surface of the first papillary muscle 42 and/or the second papillary muscle 44 being penetrated such that the port 186 is positioned adjacent the outer surface of the first papillary muscle 42 and/or the second papillary muscle 44 being penetrated.

In an alternative configuration of the mitral regurgitation treatment system, the mitral regurgitation treatment system may include an intermediate sheath 280 slidably disposed within the lumen of the outer sheath 100. The intermediate sheath 280 may include a proximal portion disposed adjacent the proximal end of the outer sheath 100, a device lumen 284 extending to a distal end 282 of the intermediate sheath 280, and an anchoring lumen 288 extending to the distal end 282 of the intermediate sheath 280. The intermediate sheath 280 may include a port 286 extending through a side wall of the device lumen 284 and/or through a side wall of the intermediate sheath 280 proximate the distal end 282 of the intermediate sheath 280.

Figure 11:
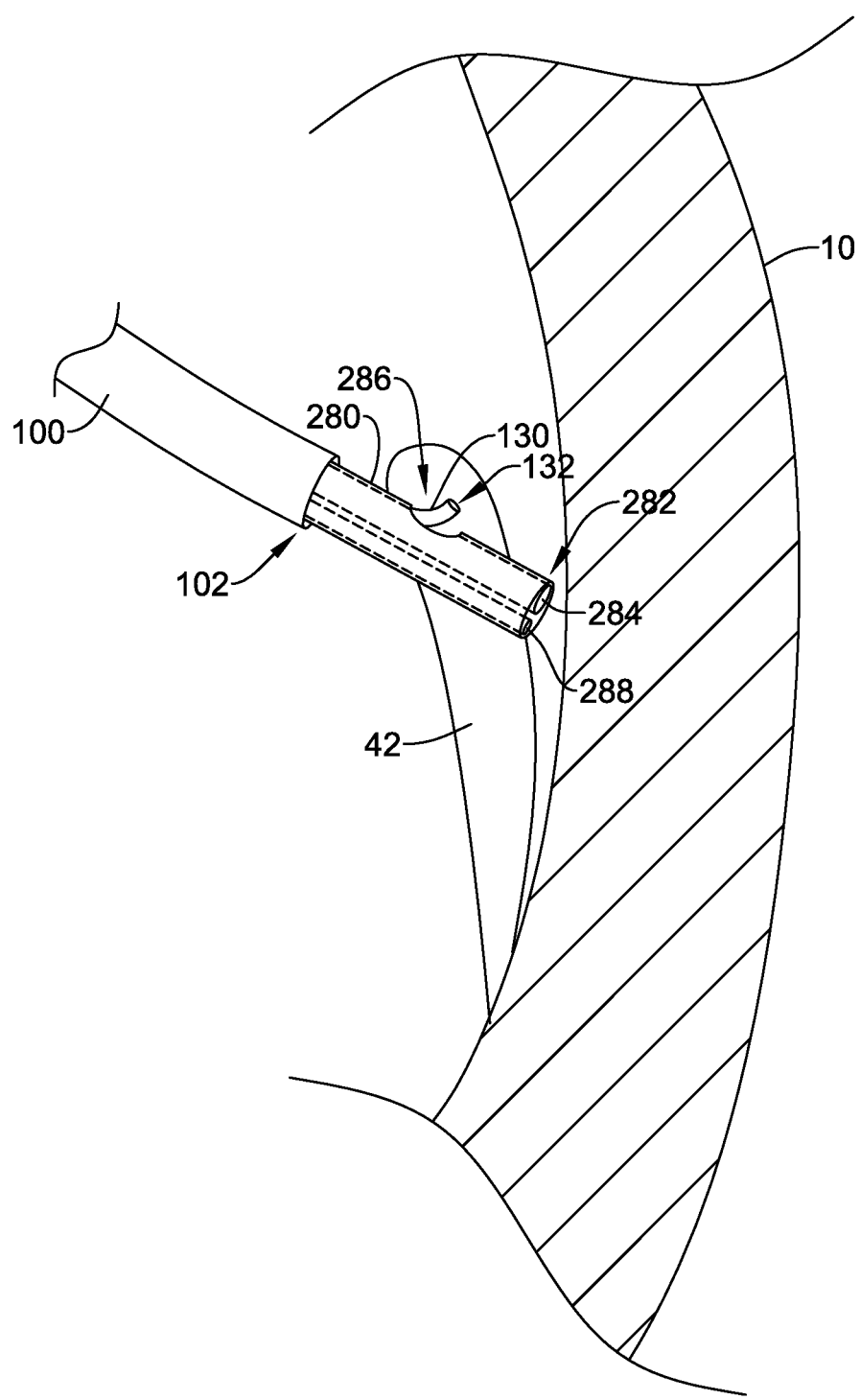
FIGS. 11 and 12 illustrate an example configuration of a mitral regurgitation treatment system.

In at least some embodiments, the distal end 282 of the intermediate sheath 280 may be a closed distal end. The inner sheath 130 may be slidably disposed within the device lumen 284 of the intermediate sheath 280. In at least some embodiments, the device lumen 284 of the intermediate sheath 280 and/or the port 286 of the intermediate sheath 280 may be configured to direct the distal end 132 of the inner sheath 130 toward and/or into contact with the first papillary muscle 42 and/or the second papillary muscle 44 upon advancement of the inner sheath 130 relative to the intermediate sheath 280. In some embodiments, the intermediate sheath 280 may be configured to cooperate with the inner sheath 130 to facilitate penetration of an anchor into the first papillary muscle 42 and/or the second papillary muscle 44 through an opening at the distal end 132 of the inner sheath 130 at an angle generally perpendicular to a surface of the first papillary muscle 42 and/or the second papillary muscle 44 being penetrated, as discussed herein. In at least some embodiments, a central longitudinal axis of the intermediate sheath 280 may be oriented substantially parallel to the outer surface of the first papillary muscle 42 and/or the second papillary muscle 44 being penetrated such that the port 286 is positioned adjacent the outer surface of the first papillary muscle 42 and/or the second papillary muscle 44 being penetrated. Additionally, the intermediate sheath 280 may be configured to be positioned with the distal end 282 of the intermediate sheath 280 proximate and/or adjacent to a wall of the heart 10, as seen in FIG. 11 for example.

Figure 12:
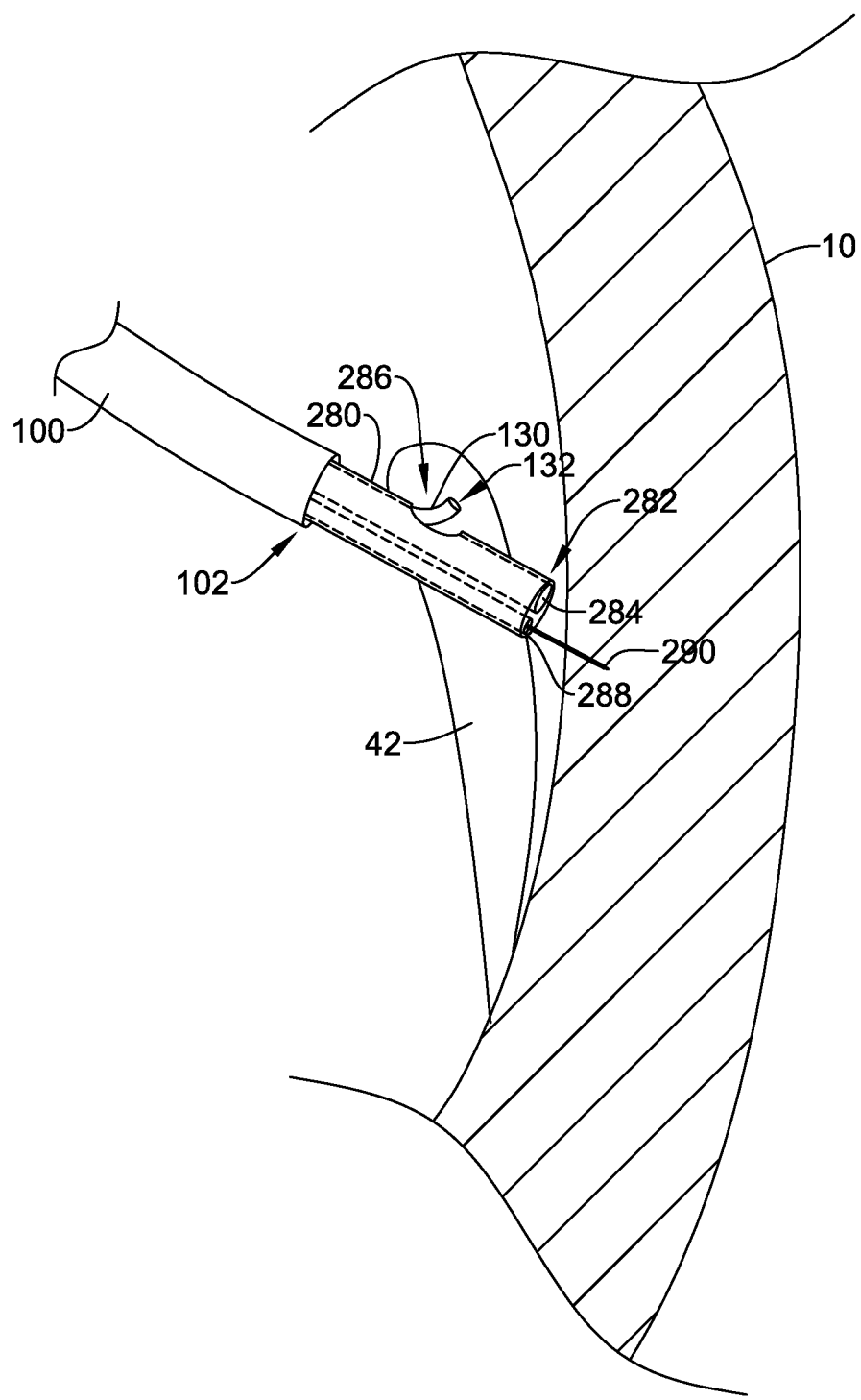

In some embodiments, the intermediate sheath 280 may include a tissue grasping mechanism 290 disposed at and/or extendable from the anchoring lumen 288 and/or the distal end 282 of the intermediate sheath 280, as seen in FIG. 12 for example. It should be understood that while aspects of the tissue grasping mechanism 290 is illustrated with respect to the first papillary muscle 42 in the interest of brevity, any and/or all aspects of the tissue grasping mechanism 290 may apply equally with respect to the second papillary muscle 44 and/or any procedures or method steps occurring with respect thereto.

In contrast to the tissue grasping mechanism 120/220/320 discussed above, the tissue grasping mechanism 290 may be configured to secure the distal end 282 of the intermediate sheath 280 relative to the wall of the heart 10 and/or the first papillary muscle 42 and/or the second papillary muscle 44 being penetrated. In some embodiments, the tissue grasping mechanism 290 may comprise a stabilizing needle configured to project distally from and/or configured to be extended out of the anchoring lumen 288 and/or the distal end 282 of the intermediate sheath 280 and into the wall of the heart 10 and/or a base of the first papillary muscle 42 and/or the second papillary muscle 44 being penetrated, as shown in FIG. 12. After extending the tissue grasping mechanism 290 and/or the stabilizing needle into the wall of the heart 10 and/or the base of the first papillary muscle 42 and/or the second papillary muscle 44 being penetrated, the inner sheath 130 may be advanced distally relative to the intermediate sheath 280 and out of the port 286 and the distal end 132 of the inner sheath 130 may be advanced into contact and/or abutment with the first papillary muscle 42 and/or the second papillary muscle 44 to facilitate penetration of the anchor into the first papillary muscle 42 and/or the second papillary muscle 44 through the opening at the distal end 132 of the inner sheath 130 at an angle generally perpendicular to the surface of the first papillary muscle 42 and/or the second papillary muscle 44 being penetrated, as discussed herein.

Figure 13:
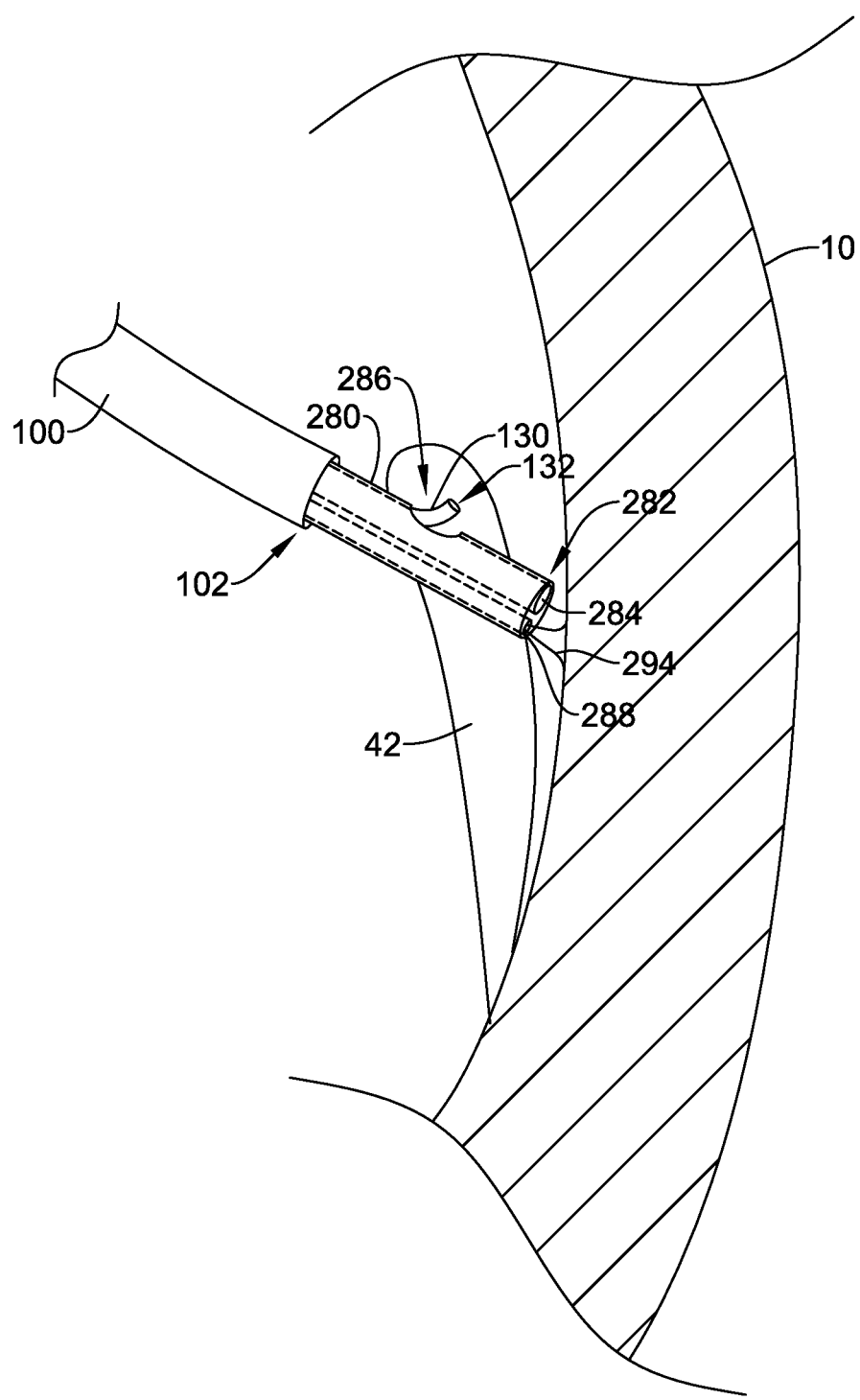
FIG. 13 illustrates an alternative configuration of the mitral regurgitation treatment system of FIGS. 11-12.

In an alternative configuration, the intermediate sheath 280 may include a tissue grasping mechanism 294 disposed at and/or extendable from the anchoring lumen 288 and/or the distal end 282 of the intermediate sheath 280, as seen in FIG. 13 for example. It should be understood that while aspects of the tissue grasping mechanism 294 is illustrated with respect to the first papillary muscle 42 in the interest of brevity, any and/or all aspects of the tissue grasping mechanism 294 may apply equally with respect to the second papillary muscle 44 and/or any procedures or method steps occurring with respect thereto.

In contrast to the tissue grasping mechanism 120/220/320 discussed above, the tissue grasping mechanism 294 may be configured to secure the distal end 282 of the intermediate sheath 280 relative to the wall of the heart 10 and/or the first papillary muscle 42 and/or the second papillary muscle 44 being penetrated, similar to the tissue grasping mechanism 290 discussed above. In some embodiments, the tissue grasping mechanism 294 may comprise a suction member configured to project distally from and/or configured to be extended out of the anchoring lumen 288 and/or the distal end 282 of the intermediate sheath 280 and into contact with the wall of the heart 10 and/or a base of the first papillary muscle 42 and/or the second papillary muscle 44 being penetrated, as shown in FIG. 13. The tissue grasping mechanism 294 and/or the suction member may expand radially outward in a distal direction, and the tissue grasping mechanism 294 and/or the suction member may have a generally conical or trumpet-like shape expanding to a greater outer extent further from the distal end 282 of the intermediate sheath 280.

After extending the tissue grasping mechanism 294 and/or the suction member into contact with the wall of the heart 10 and/or the base of the first papillary muscle 42 and/or the second papillary muscle 44 being penetrated, suction and/or negative pressure may be applied to the anchoring lumen 288 and/or the tissue grasping mechanism 294 and/or the suction member, thereby securing the tissue grasping mechanism 294 and/or the suction member and/or the intermediate sheath 280 to the wall of the heart 10 and/or the base of the first papillary muscle 42 and/or the second papillary muscle 44 being penetrated. Subsequently, the inner sheath 130 may be advanced distally relative to the intermediate sheath 280 and out of the port 286 and the distal end 132 of the inner sheath 130 may be advanced into contact and/or abutment with the first papillary muscle 42 and/or the second papillary muscle 44 to facilitate penetration of the anchor into the first papillary muscle 42 and/or the second papillary muscle 44 through the opening at the distal end 132 of the inner sheath 130 at an angle generally perpendicular to the surface of the first papillary muscle 42 and/or the second papillary muscle 44 being penetrated, as discussed herein.

Figure 14:
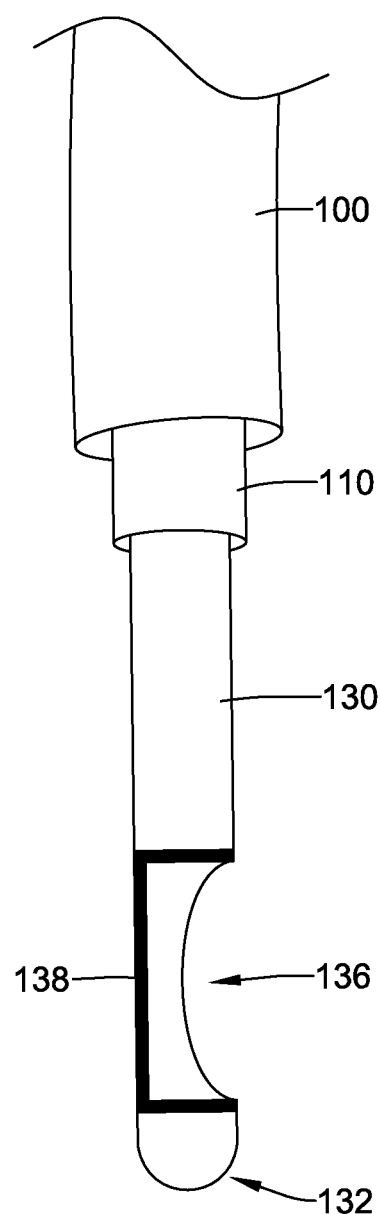
FIGS. 14 and 15 illustrate example configurations of the mitral regurgitation treatment system of FIG. 9.
Figure 15:
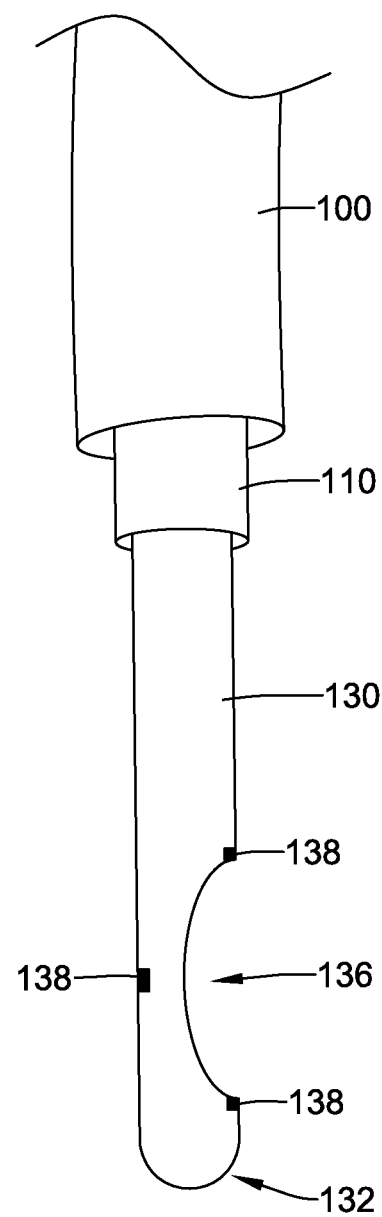

Additionally, in at least some embodiments, the inner sheath 130 may include at least one orientation marker 138 positioned adjacent the port 136 for determining an orientation of the port 136 relative to the first papillary muscle 42 and/or the second papillary muscle 44, as seen in FIGS. 14 and 15. While not discussed in detail, it is contemplated that the positioning sheath 180 and/or the intermediate sheath 280 may similarly include at least one orientation marker 138 positioned adjacent the port 186 and/or the port 286, respectively, for determining an orientation of the portion 186/286 relative to the first papillary muscle 42 and/or the second papillary muscle 44, and any discussion related to the at least one orientation marker 138 and/or the port 136 may be applied equally to any and/or all embodiments having a port (e.g., 186, 286) through a side wall of a sheath or lumen.

In some embodiments, the at least one orientation marker 138 may be radiopaque for identification during imaging. In some embodiments, the at least one orientation marker 138 may comprise and/or may be a single orientation marker 138 framing or outlining the port 136 as viewed from a side of the inner sheath 130, as shown in FIG. 14. The at least one orientation marker 138 may be distinguishable under imaging to determine the position of the inner sheath 130 and the port 136 relative to the first papillary muscle 42 and/or the second papillary muscle 44. For example, the at least one orientation marker 138 may include three sides or legs, wherein a longest side or leg of the at least one orientation marker 138 may be oriented parallel with the central longitudinal axis of the inner sheath 130, and a shorter pair of sides or legs of the at least one orientation marker 138 may be oriented transversely relative to the central longitudinal axis of the inner sheath 130.

In an alternative configuration, the at least one orientation marker 138 may comprise and/or may be three or more individual orientation markers 138 framing or outlining the port 136 as viewed from the side of the inner sheath 130, as shown in FIG. 15. The at least one orientation marker 138 may be distinguishable under imaging to determine the position of the inner sheath 130 and the port 136 relative to the first papillary muscle 42 and/or the second papillary muscle 44. For example, one orientation marker 138 may be disposed on and/or within the side wall of the inner sheath 130 opposite the port 136, which two or more orientation markers 138 may be disposed on and/or within the side wall of the inner sheath 130 adjacent to and/or around an edge or circumference of the port 136. Other orientation marker configurations—for example, L-shaped, circular, etc. —are also contemplated.

Figure 16:
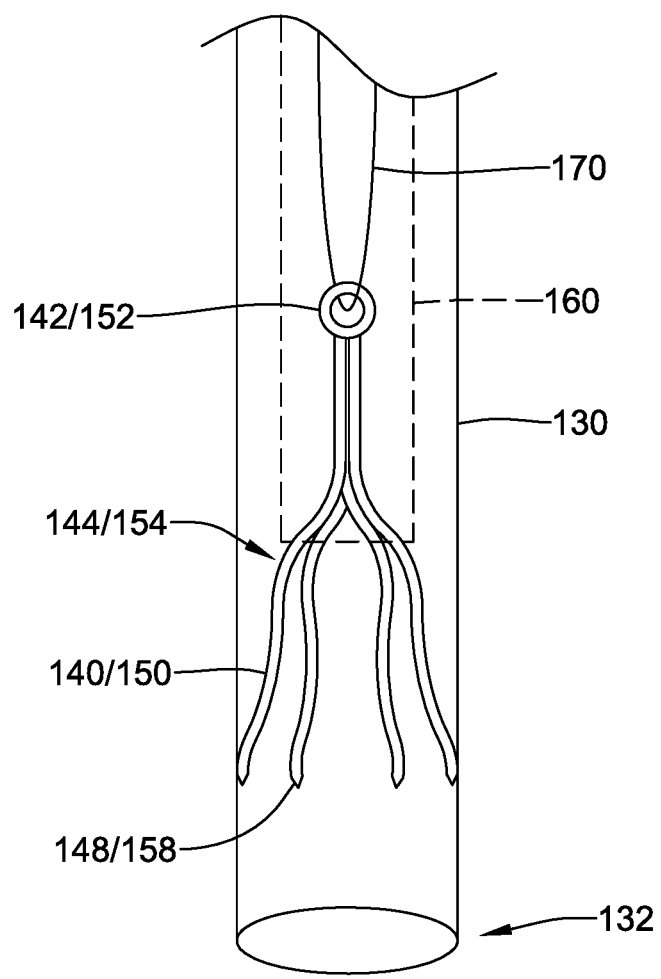
FIG. 16 illustrates an example anchor in a delivery configuration.
Figure 17:
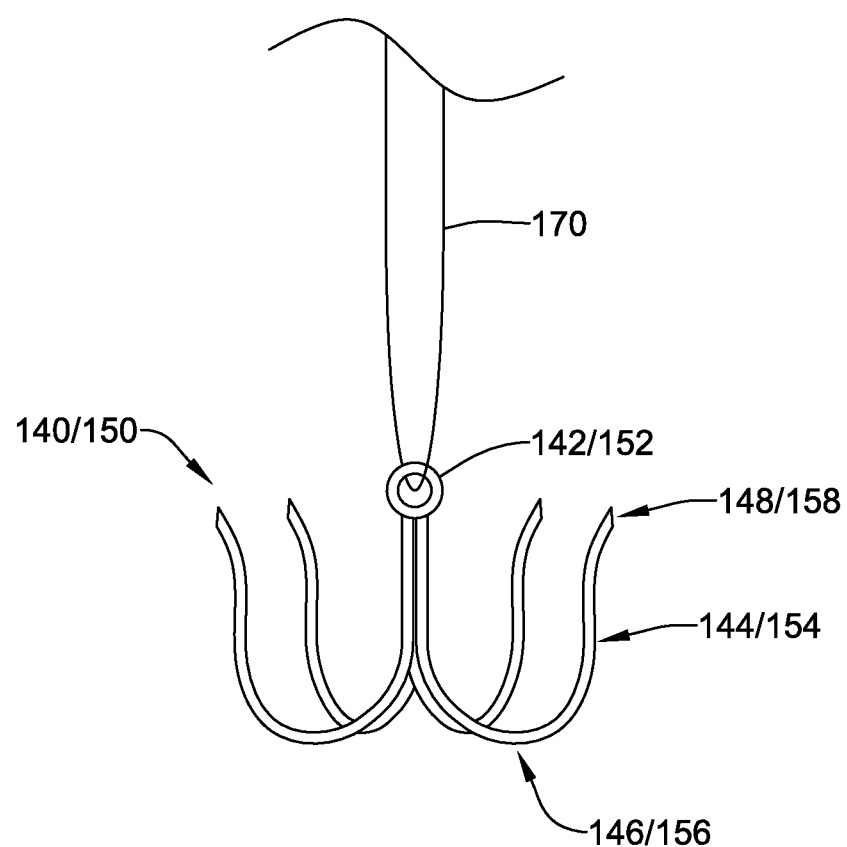
FIG. 17 illustrates the example anchor of FIG. 16 in a deployed configuration.

FIGS. 16 and 17 illustrate an example of a first/second anchor 140/150 suitable for use with the disclosed mitral regurgitation treatment system(s). It shall be understood that the first/second anchor 140/150 may be used with any and/or all of the devices disclosed herein, as well as others. Furthermore, one or more additional anchors may be used in some embodiments. The first/second anchor 140/150 may include an eyelet 142/152 and a plurality of anchor legs 144/154 extending from the eyelet 142/152. In at least some embodiments, the plurality of anchor legs 144/154 may extend from the eyelet 142/152 to free ends 148/158, the free ends 148/158 each having a tip configured to penetrate tissue. In some embodiments, the tip of each free end 148/158 may be pointed and/or sharpened to easily pierce tissue. In some embodiments, the tip of each free end 148/158 may be slightly rounded, but still capable of easily piercing tissue without tearing said tissue. Combinations and/or other configurations of the tip are also contemplated. The first/second anchor 140/150 may be configured to penetrate and secure to the first papillary muscle 42 and/or the second papillary muscle 44.

The first/second anchor 140/150 and/or the plurality of anchor legs 144/154 may be configured to shift from a delivery configuration when constrained by the inner sheath 130, wherein the plurality of anchor legs 144/154 is generally straightened and extends longitudinally away from the eyelet 142/152 in a first direction, and a deployed configuration when unconstrained by the inner sheath 130, wherein the plurality of anchor legs 144/154 extends in the first direction away from the eyelet 142/152 and then curves back on itself at a bend location 146/156 to extend in a second direction opposite the first direction from the bend location 146/156 to free ends 148/158. In at least some embodiments, the first direction may be a distal direction and the second direction may be a proximal direction. In some embodiments, the plurality of anchor legs 144/154 may extend in the second direction from the bend location 146/156 until the tip of each free end 148/158 is proximate to the eyelet 142/152 in the deployed configuration. For example, in the delivery configuration, the free ends 148/158 of the plurality of anchor legs 144/154 may point in a distal direction, and in the deployed configuration, the free ends 148/158 of the plurality of anchor legs 144/154 may point in a proximal direction.

In some embodiments, the first/second anchor 140/150 may be biased towards the deployed configuration when unconstrained. In some embodiments, the first/second anchor 140/150 may be self-biased towards the deployed configuration with unconstrained. In at least some embodiments, the first/second anchor 140/150 may be formed from a shape memory material. Some suitable but non-limiting materials for the first/second anchor 140/150, for example metallic materials, polymer materials, composite materials, synthetic materials, etc., are described below.

As shown in FIG. 16, the mitral regurgitation treatment system may comprise an inner sheath 130 including a first anchor 140 disposed within a lumen of an inner sheath 130 in the delivery configuration. The first anchor 140 may be configured to penetrate and secure to the first papillary muscle 42. In at least some embodiments, the mitral regurgitation treatment system may include a pusher member 160 (shown in FIG. 16 in phantom) slidably disposed within the lumen of the inner sheath 130. The pusher member 160 may be configured to expel the first anchor 140 from the lumen of the inner sheath 130 and/or to push/urge the first anchor 140 into the first papillary muscle 42. In some embodiments, a proximal portion and/or the eyelet 142 of the first anchor 140 may be disposed within a lumen of the pusher member 160 in the delivery configuration. The tissue grasping mechanism 120/220/320 may be configured to hold and stabilize the first papillary muscle 42 for penetration and securement of the first anchor 140 to the first papillary muscle 42. The inner sheath 130 may further include a tethering element 170 disposed within the lumen of the inner sheath 130 and/or within a lumen of the pusher member 160. The tethering element 170 may engage with and/or be attached to the eyelet 142 of the first anchor 140. The tethering element 170 may extend proximally from the eyelet 142 of the first anchor 140. The tethering element 170 may take one or more of various forms known in the art—including, but not limited to, a suture, a filament, a wire, etc.

The inner sheath 130 may be configured to extend and/or be advanced distally out of the distal end 112 of the intermediate sheath 110 and into contact and/or engagement with the first papillary muscle 42 and/or the second papillary muscle 44. The inner sheath 130 may be configured to extend and/or be advanced distally out of the distal end 112 of the intermediate sheath 110 while the tissue grasping mechanism 120/220/320/290/294 holds and stabilizes the first papillary muscle 42 and/or the second papillary muscle 44 and/or the distal end 282 of the intermediate sheath 280 to ensure proper positioning of a distal end 132 of the inner sheath 130 relative to the first papillary muscle 42 and/or the second papillary muscle 44 (e.g., FIGS. 4, 6, and 8-13). Upon exiting the inner sheath 130, the first anchor 140 may be configured to shift toward the deployed configuration, shown in FIG. 17 for example.

In some embodiments, the inner sheath 130 may further include a second anchor 150 advanceable through the lumen of the inner sheath 130. The second anchor 150 may be configured to penetrate and secure to the second papillary muscle 44. The tissue grasping mechanism 120/220/320/290/294 may be configured to hold and stabilize the second papillary muscle 44 and/or the distal end 282 of the intermediate sheath 280 for penetration and securement of the second anchor 150 to the second papillary muscle 44. In some embodiments, the first anchor 140 and the second anchor 150 may be advanceable through the inner sheath 130 in series. In some embodiments, the first anchor 140 and the second anchor 150 may be advanceable through the inner sheath 130 in parallel. In some embodiments, the first anchor 140 and the second anchor 150 may be advanceable through the inner sheath 130 separately. In some embodiments, the first anchor 140 and the second anchor 150 may be advanceable through the inner sheath 130 together.

The first anchor 140 and the second anchor 150 may be connectable to each other. In some embodiments, the first anchor 140 and the second anchor 150 may be configured to be connected to each other after deployment from the inner sheath 130. In some embodiments, the first anchor 140 and the second anchor 150 may be connected to each other by the tethering element 170. The tethering element 170 may engage with and/or be attached to the eyelet 152 of the second anchor 150. The tethering element 170 may extend proximally from the eyelet 152 of the second anchor 150. In some embodiments, the tethering element 170 may be configured to extend between the first papillary muscle 42 and the second papillary muscle 44, and/or the eyelet 142 of the first anchor 140 and the eyelet 152 of the second anchor 150, in tension. In some embodiments, at least a portion of each of the first anchor 140 and the second anchor 150 is configured to extend transversely relative to the tethering element 170 when unconstrained by the inner sheath 130. In some embodiments, the first anchor 140 and the second anchor 150 may each include a separate and/or independent tethering element, and the separate and/or independent tethering elements may be connectable together. For example, the tethering element of the first anchor 140 may be connectable to the tethering element of the second anchor 150, such as by tying, adhesive(s), or other suitable means.

Figure 18:
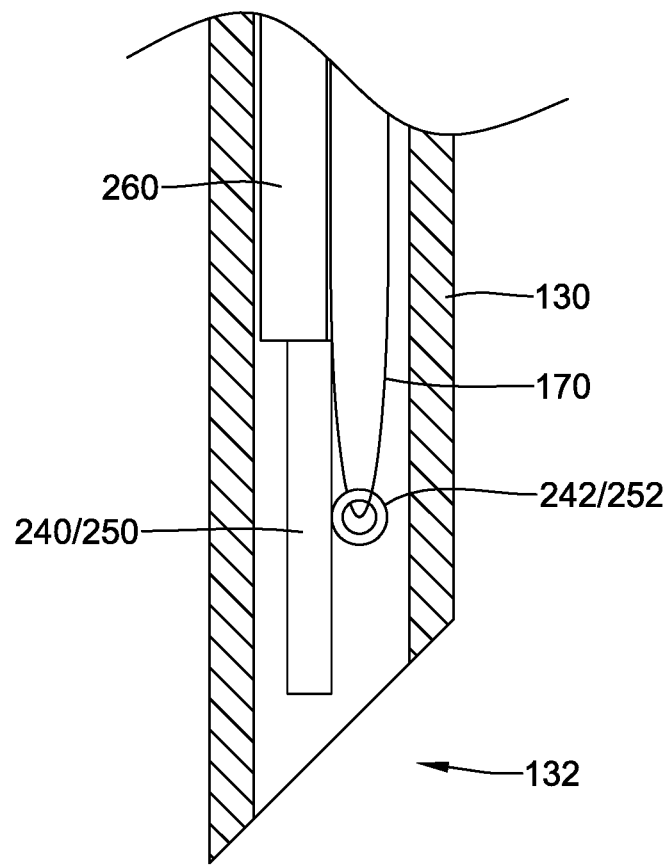
FIG. 18 illustrates an alternative anchor in the delivery configuration.

FIG. 18 illustrates an alternative first/second anchor 240/250 disposed within the lumen of the inner sheath 130 in a delivery configuration. The distal end 132 of the inner sheath 130 may be configured to penetrate the first papillary muscle 42 and/or the second papillary muscle 44 in order to deploy the first/second anchor 240/250. In the delivery configuration, the first/second anchor 240/250 may be oriented generally parallel to a central longitudinal axis of the inner sheath 130 and/or generally perpendicular to the outer surface of the first papillary muscle 42 and/or the second papillary muscle 44. Alternatively, the first/second anchor 240/250 may be shaped and/or configured to pierce tissue as the first/second anchor 240/250 is advanced out of the distal end 132 of the inner sheath 130. Some suitable but non-limiting materials for the first/second anchor 240/250, for example metallic materials, polymer materials, composite materials, synthetic materials, etc., are described below.

A pusher member 260 may be slidably disposed within the lumen of the inner sheath 130. In some embodiments, the pusher member 260 may be an elongate solid rod or shaft, however, other configurations are also contemplated. The pusher member 260 may be configured to expel the first/second anchor 240/250 from the lumen of the inner sheath 130. After exiting the lumen of the inner sheath 130, the first/second anchor 240/250 may be configured to shift to a deployed configuration, wherein the first/second anchor 240/250 is oriented generally perpendicular to the central longitudinal axis of the inner sheath 130 and/or generally parallel to and/or abutting the outer surface of the first papillary muscle 42 and/or the second papillary muscle 44. The tethering element 170 may extend from an eyelet 242/252 of the first/second anchor 240/250. Upon deployment, the tethering element 170 may extend through the first papillary muscle 42 and/or the second papillary muscle 44.

In some embodiments, the tethering element 170 may be configured to extend between the first papillary muscle 42 and the second papillary muscle 44, and/or the first anchor 240 and the second anchor 250, in tension. In some embodiments, the tethering element 170 may be configured to extend between the eyelet 242 of the first anchor 240 and the eyelet 252 of the second anchor 250, in tension. In some embodiments, at least a portion of each of the first anchor 240 and the second anchor 250 is configured to extend transversely relative to the tethering element 170 when unconstrained by the inner sheath 130. In some embodiments, the first anchor 240 and the second anchor 250 may each include a separate and/or independent tethering element, and the separate and/or independent tethering elements may be connectable together. For example, the tethering element of the first anchor 240 may be connectable to the tethering element of the second anchor 250, such as by tying, adhesive(s), or other suitable means.

A method for treating mitral regurgitation may include advancing the distal end 102 of the outer sheath 100 intravascularly to the left ventricle 40 of the heart 10, as shown in FIG. 2 and described herein. The distal end 102 of the outer sheath 100 may be positioned proximate the first papillary muscle 42. The method may include advancing the intermediate sheath 110/280 and/or the tissue grasping mechanism 120/220/320/290/294 out of the distal end 102 of the outer sheath 100 and into engagement with the first papillary muscle 42. The method may include grasping the first papillary muscle 42 of the left ventricle 40 using the tissue grasping mechanism 120/220/320/290/294, the tissue grasping mechanism 120/220/320/290/294 being configured to hold and stabilize the first papillary muscle 42 for penetration of the first anchor 140/240 into the first papillary muscle 42 from the inner sheath 130, the inner sheath 130 being slidably disposed within the lumen of the intermediate sheath 110/280.

Figure 19:
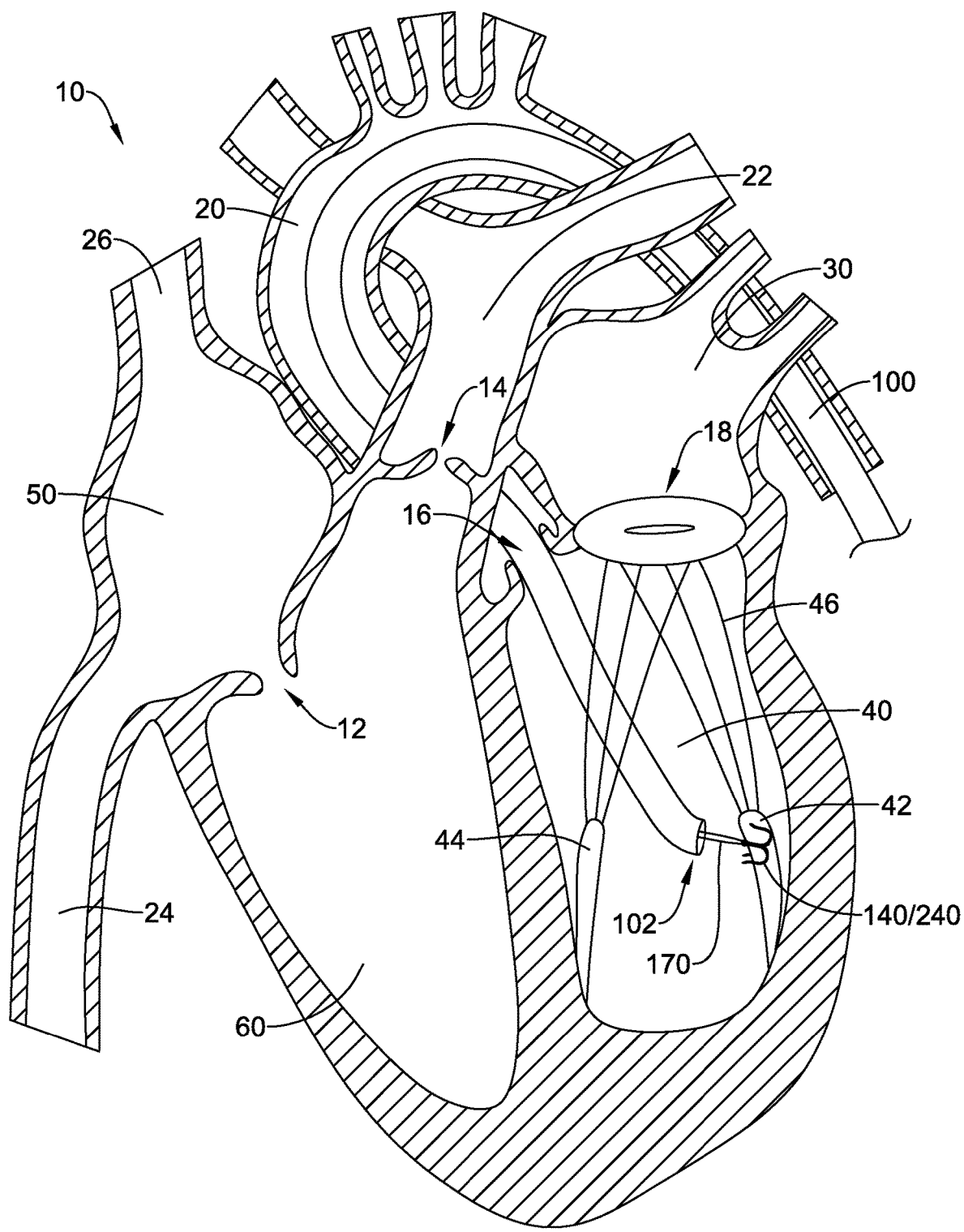
FIGS. 19-22 illustrate further aspects of the example method of treating mitral regurgitation.

In some embodiments, the method may include advancing the inner sheath 130 through the lumen of the intermediate sheath 110/280 and/or out of the distal end 112/282 of the intermediate sheath 110/280 proximate the first papillary muscle 42 while the tissue grasping mechanism 120/220/320/290/294 holds and stabilizes the first papillary muscle 42 relative to the outer sheath 100 and/or a wall of the left ventricle 40. The method may include advancing the first anchor 140/240 into the first papillary muscle 42 from within a lumen of the inner sheath 130, the first anchor 140/240 being configured to penetrate and secure to the first papillary muscle 42 of the left ventricle 40. The tethering element 170 may extend from the first anchor 140/240 into the distal end 132 of the inner sheath 130 and/or the distal end 102 of the outer sheath 100. The method may include releasing the first papillary muscle 42 of the left ventricle 40 from the tissue grasping mechanism 120/220/320/290/294 and/or withdrawing the tissue grasping mechanism 120/220/320/290/294 and/or the intermediate sheath 110/280 into the distal end 102 of the outer sheath 100, as seen in FIG. 19 for example.

Figure 20:
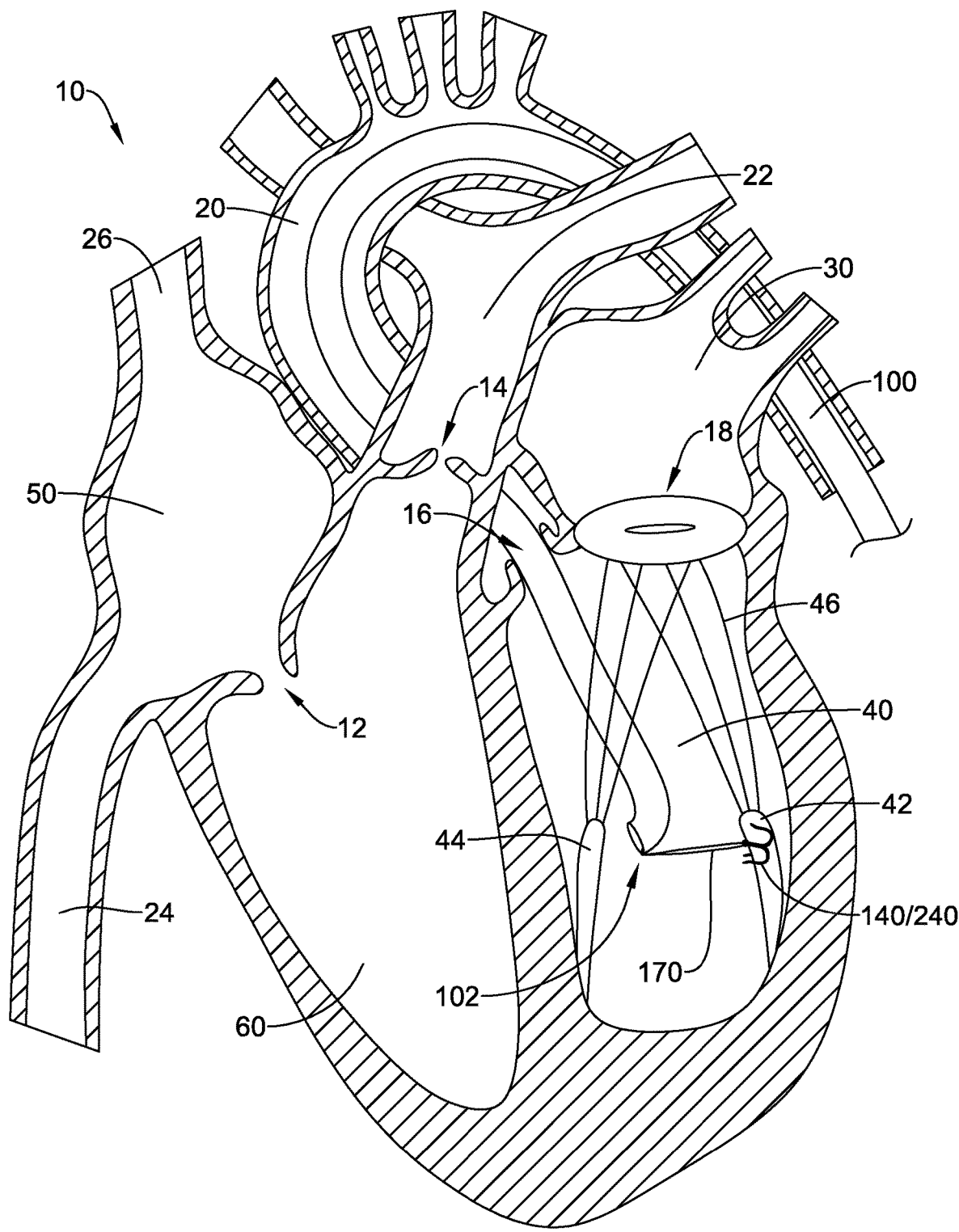

The method may include repositioning the distal end 102 of the outer sheath 100 adjacent the second papillary muscle 44 of the left ventricle 40, as shown in FIG. 20. The method may include advancing the intermediate sheath 110/280 and/or the tissue grasping mechanism 120/220/320/290/294 out of the distal end 102 of the outer sheath 100 and into engagement with the second papillary muscle 44. The method may include grasping the second papillary muscle 44 of the left ventricle 40 using the tissue grasping mechanism 120/220/320/290/294, the tissue grasping mechanism 120/220/320/290/294 being configured to hold and stabilize the second papillary muscle 44 for penetration of the second anchor 150/250 into the second papillary muscle 44 from the inner sheath 130.

Figure 21:
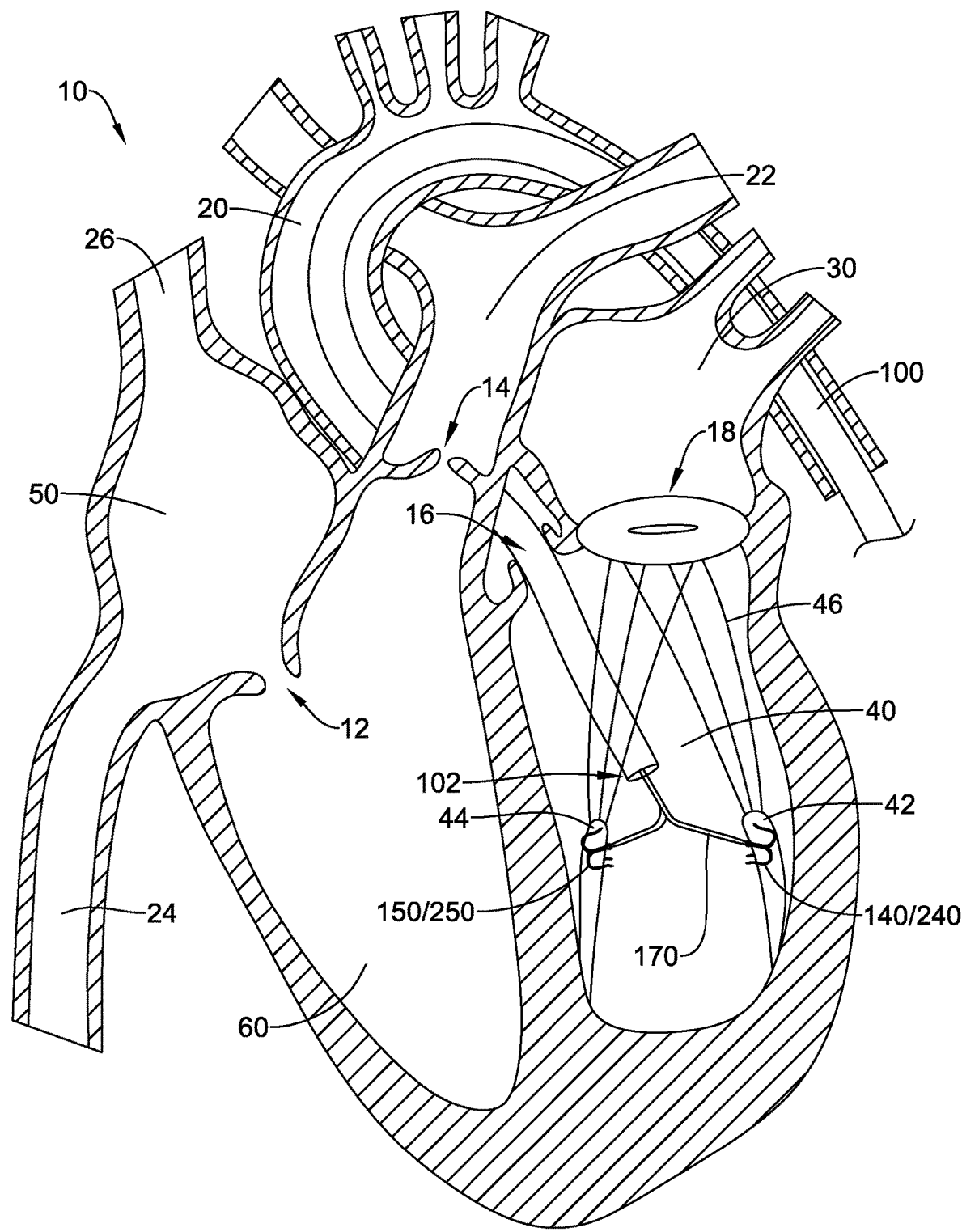

In some embodiments, the method may include advancing the inner sheath 130 through the lumen of the intermediate sheath 110/280 and/or out of the distal end 112 of the intermediate sheath 110 proximate the second papillary muscle 44 while the tissue grasping mechanism 120/220/320/290/294 holds and stabilizes the second papillary muscle 44 relative to the outer sheath 100 and/or a wall of the left ventricle 40. The method may include advancing the second anchor 150/250 into the second papillary muscle 44 from within a lumen of the inner sheath 130, the second anchor 150/250 being configured to penetrate and secure to the second papillary muscle 44 of the left ventricle 40. The tethering element 170 may extend from the second anchor 150/250 into the distal end 132 of the inner sheath 130 and/or the distal end 102 of the outer sheath 100, and/or the tethering element 170 may extend between the first anchor 140/240 and the second anchor 150/250. The method may include releasing the second papillary muscle 44 of the left ventricle 40 from the tissue grasping mechanism 120/220/320/290/294 and/or withdrawing the tissue grasping mechanism 120/220/320/290/294 and/or the intermediate sheath 110/280 into the distal end 102 of the outer sheath 100, as seen in FIG. 21 for example.

Figure 22:
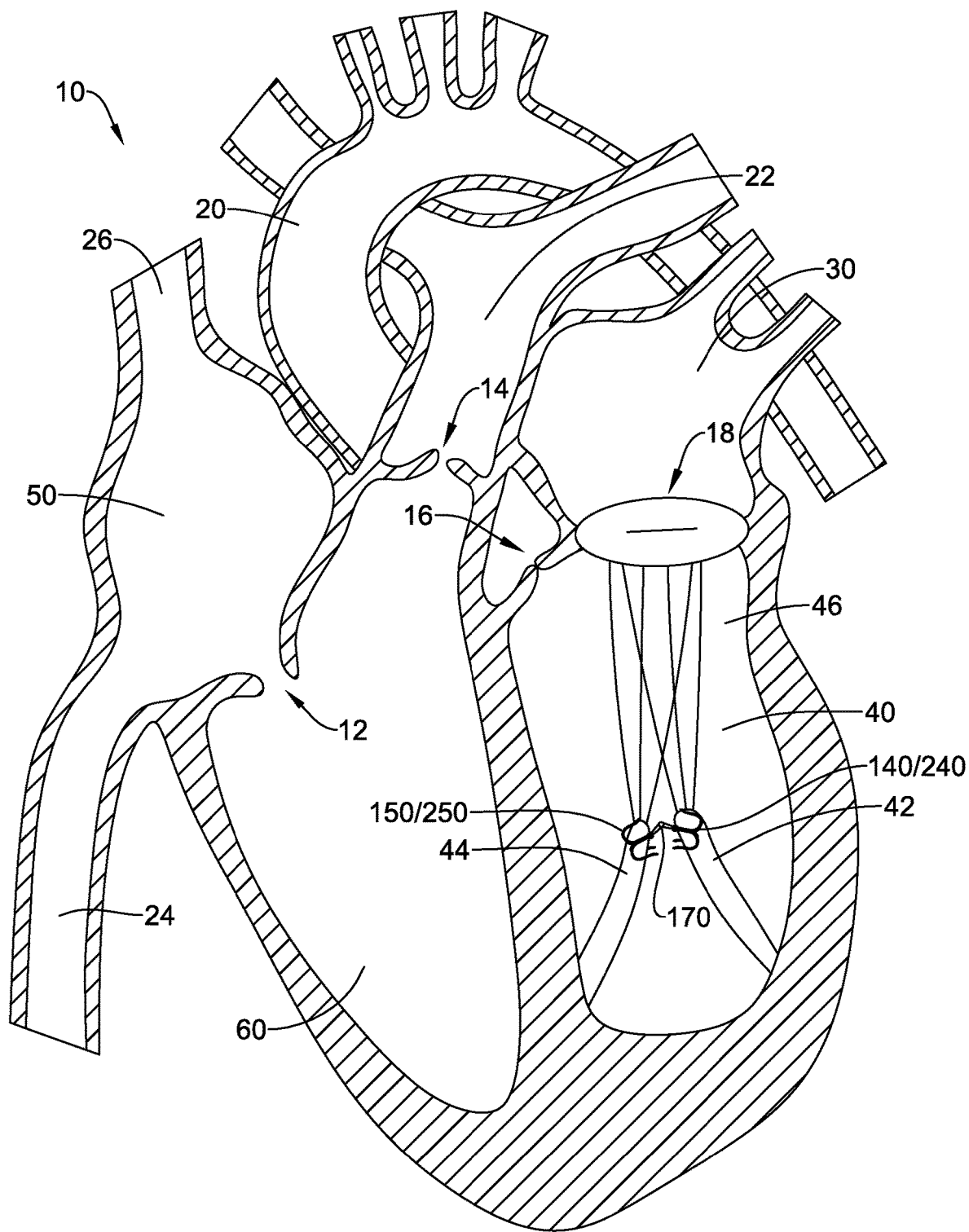

In some embodiments, the method may include translating the first papillary muscle 42 closer to the second papillary muscle 44 by tensioning the tethering element 170 between the first anchor 140/240 and the second anchor 150/250, as seen in FIG. 22. In some embodiments, the mitral regurgitation treatment system the tethering element 170 may draw, translate, and/or relocate the first papillary muscle 42 into contact with the second papillary muscle 44. For example, in some embodiments, a space between the first papillary muscle 42 and the second papillary muscle 44 may be eliminated and/or reduced to zero. This arrangement and/or configuration may be equally applied to any configuration and/or embodiment disclosed herein.

In some embodiments, the method may include connecting the tethering element of the first anchor 140/240 to the tethering element of the second anchor 140/240, as discussed herein, such as by tying the tethering element of the first anchor 140/240 together with the tethering element of the second anchor 140/240, or by fixing the tethering element of the first anchor 140/240 to the tethering element of the second anchor 140/240 with an adhesive, or by other suitable means.

The materials that can be used for the various components of the outer sheath 100, the intermediate sheath 110/280, the tissue grasping mechanism 120/220/320/290/294, the inner sheath 130, the first anchor 140/240, the second anchor 150/250, the pusher member 160/260, the tethering element 170, the positioning sheath 180, etc. (and/or other systems or components disclosed herein) and the various elements thereof disclosed herein may include those commonly associated with medical devices. For simplicity purposes, the following discussion makes reference to the outer sheath 100, the intermediate sheath 110/280, the tissue grasping mechanism 120/220/320/290/294, the inner sheath 130, the first anchor 140/240, the second anchor 150/250, the pusher member 160/260, the tethering element 170, the positioning sheath 180, etc. However, this is not intended to limit the devices and methods described herein, as the discussion may be applied to other elements, members, components, or devices disclosed herein, such as, but not limited to, the first prong 122/222, the second prong 124/224, the curved member 322, the plurality of anchor legs 144/154, etc. and/or elements or components thereof.

In some embodiments, the outer sheath 100, the intermediate sheath 110/280, the tissue grasping mechanism 120/220/320/290/294, the inner sheath 130, the first anchor 140/240, the second anchor 150/250, the pusher member 160/260, the tethering element 170, the positioning sheath 180, etc., and/or components thereof may be made from a metal, metal alloy, polymer (some examples of which are disclosed below), a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; platinum; palladium; gold; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the outer sheath 100, the intermediate sheath 110/280, the tissue grasping mechanism 120/220/320/290/294, the inner sheath 130, the first anchor 140/240, the second anchor 150/250, the pusher member 160/260, the tethering element 170, the positioning sheath 180, etc., and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the outer sheath 100, the intermediate sheath 110/280, the tissue grasping mechanism 120/220/320/290/294, the inner sheath 130, the first anchor 140/240, the second anchor 150/250, the pusher member 160/260, the tethering element 170, the positioning sheath 180, etc. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the outer sheath 100, the intermediate sheath 110/280, the tissue grasping mechanism 120/220/320/290/294, the inner sheath 130, the first anchor 140/240, the second anchor 150/250, the pusher member 160/260, the tethering element 170, the positioning sheath 180, etc. to achieve the same result.

In some embodiments, a degree of Magnetic Resonance Imaging (MRI) compatibility is imparted into the outer sheath 100, the intermediate sheath 110/280, the tissue grasping mechanism 120/220/320/290/294, the inner sheath 130, the first anchor 140/240, the second anchor 150/250, the pusher member 160/260, the tethering element 170, the positioning sheath 180, etc. For example, the outer sheath 100, the intermediate sheath 110/280, the tissue grasping mechanism 120/220/320/290/294, the inner sheath 130, the first anchor 140/240, the second anchor 150/250, the pusher member 160/260, the tethering element 170, the positioning sheath 180, etc., and/or components or portions thereof, may be made of a material that does not substantially distort the image and create substantial artifacts (e.g., gaps in the image). Certain ferromagnetic materials, for example, may not be suitable because they may create artifacts in an MRI image. The outer sheath 100, the intermediate sheath 110/280, the tissue grasping mechanism 120/220/320/290/294, the inner sheath 130, the first anchor 140/240, the second anchor 150/250, the pusher member 160/260, the tethering element 170, the positioning sheath 180, etc., or portions thereof, may also be made from a material that the MM machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the outer sheath 100, the intermediate sheath 110/280, the tissue grasping mechanism 120/220/320/290/294, the inner sheath 130, the first anchor 140/240, the second anchor 150/250, the pusher member 160/260, the tethering element 170, the positioning sheath 180, etc., and/or portions thereof, may be made from or include a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments, the sheath can be blended with a liquid crystal polymer (LCP). For example, the mixture can contain up to about 6 percent LCP.

In some embodiments, the outer sheath 100, the intermediate sheath 110/280, the tissue grasping mechanism 120/220/320/290/294, the inner sheath 130, the first anchor 140/240, the second anchor 150/250, the pusher member 160/260, the tethering element 170, the positioning sheath 180, etc. may include and/or be formed from a textile material. Some examples of suitable textile materials may include synthetic yarns that may be flat, shaped, twisted, textured, pre-shrunk or un-shrunk. Synthetic biocompatible yarns suitable for use in the present invention include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun-types. The type and denier of the yarn chosen may be selected in a manner which forms a biocompatible and implantable prosthesis and, more particularly, a vascular structure having desirable properties.

In some embodiments, the outer sheath 100, the intermediate sheath 110/280, the tissue grasping mechanism 120/220/320/290/294, the inner sheath 130, the first anchor 140/240, the second anchor 150/250, the pusher member 160/260, the tethering element 170, the positioning sheath 180, etc. may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); antiproliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A system for treating mitral regurgitation, comprising:
    an outer sheath having a lumen extending to a distal end of the outer sheath;
    an intermediate sheath slidably disposed within the lumen of the outer sheath, the intermediate sheath having a lumen extending to a distal end of the intermediate sheath; and
    an inner sheath slidably disposed within the lumen of the intermediate sheath, wherein the inner sheath includes a first anchor disposed within a lumen of the inner sheath, the first anchor being configured to penetrate and secure to a first papillary muscle;
    wherein the intermediate sheath includes a tissue grasping mechanism at the distal end of the intermediate sheath, the tissue grasping mechanism being configured to hold and stabilize the first papillary muscle for penetration and securement of the first anchor to the first papillary muscle.

2. The system of claim 1, wherein the tissue grasping mechanism includes a first prong and a second prong each attached to the distal end of the intermediate sheath;
    wherein the first prong and the second prong are configured to shift between a grasping configuration and an open configuration, the first prong and the second prong being biased toward the open configuration when unconstrained.

3. The system of claim 2, wherein in the open configuration, a gap between a distal end of the first prong and a distal end of the second prong is greater than an outer extent of the outer sheath.

4. The system of claim 3, wherein relative translation of the outer sheath and the tissue grasping mechanism toward each other urges the first prong and the second prong toward the grasping configuration.

5. The system of claim 4, wherein the intermediate sheath includes an actuator element extending proximally from the tissue grasping mechanism to an actuation position proximate a proximal end of the intermediate sheath.

6. The system of claim 5, wherein tension applied to the actuator element urges the first prong and the second prong toward the grasping configuration.

7. The system of claim 1, wherein the tissue grasping mechanism includes a curved member attached to the distal end of the intermediate sheath, the curved member being configured to extend around a majority of a circumference of the first papillary muscle.

8. The system of claim 7, wherein distal advancement of the inner sheath relative to the curved member until a distal end of the inner sheath is positioned against the first papillary muscle grasps the first papillary muscle to facilitate penetration of the first anchor into the first papillary muscle through the distal end of the inner sheath.

9. The system of claim 7, wherein the inner sheath includes a port extending through a side wall of the inner sheath proximate a distal end of the inner sheath, and at least one orientation marker positioned adjacent the port for determining an orientation of the port relative to the first papillary muscle;
    wherein distal advancement of the inner sheath relative to the curved member until the distal end of the inner sheath is positioned adjacent the first papillary muscle grasps the first papillary muscle to facilitate penetration of the first anchor into the first papillary muscle through the port at an angle generally perpendicular to a surface of the first papillary muscle being penetrated.

10. The system of claim 9, wherein the distal end of the inner sheath is a closed distal end.

11. A system for treating mitral regurgitation, comprising:

an outer sheath having a lumen extending to a distal end of the outer sheath;

an intermediate sheath slidably disposed within the lumen of the outer sheath, the intermediate sheath having a lumen extending to a distal end of the intermediate sheath;

an inner sheath slidably disposed within the lumen of the intermediate sheath, wherein the inner sheath includes a first anchor disposed within a lumen of the inner sheath, the first anchor being configured to penetrate and secure to a first papillary muscle;

wherein the intermediate sheath includes a tissue grasping mechanism at the distal end of the intermediate sheath, the tissue grasping mechanism being configured to hold and stabilize the first papillary muscle for penetration and securement of the first anchor to the first papillary muscle; and a second anchor advanceable through the lumen of the inner sheath, the second anchor being configured to penetrate and secure to a second papillary muscle.

12. The system of claim 11, wherein the first anchor and the second anchor are connectable to each other.

13. The system of claim 12, wherein the first anchor and the second anchor are configured to be connected to each other after deployment from the inner sheath.

14. The system of claim 12, wherein the first anchor and the second anchor are connected to each other by a tethering element.

15. The system of claim 11, wherein the tissue grasping mechanism is configured to hold and stabilize the second papillary muscle for penetration and securement of the second anchor to the second papillary muscle.

* * * * *